US008501089B2

(12) United States Patent
Herdt et al.

(10) Patent No.: US 8,501,089 B2
(45) **Date of Patent: *Aug. 6, 2013**

(54) METHODS OF DISINFECTING PACKAGES IN ASEPTIC PACKAGING USING ANTIMICROBIAL PERACID COMPOSITIONS WITH SELECTED CATALASE ENZYMES

(75) Inventors: Brandon L. Herdt, Hastings, MN (US); Joshua P. Magnuson, South St. Paul, MN (US); David D. McSherry, St. Paul, MN (US); Junzhong Li, Apple Valley, MN (US); Krista L. Owens, Apple Valley, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/528,037

(22) Filed: Jun. 20, 2012

(65) Prior Publication Data

US 2012/0321510 A1 Dec. 20, 2012

Related U.S. Application Data

(63) Continuation of application No. 12/185,200, filed on Aug. 4, 2008, now Pat. No. 8,226,939.

(60) Provisional application No. 61/046,232, filed on Apr. 18, 2008.

(51) Int. Cl.

| | |
|---|---|
| ***A61L 9/00*** | (2006.01) |
| ***A61K 38/43*** | (2006.01) |
| ***C12N 9/00*** | (2006.01) |
| ***C12N 1/20*** | (2006.01) |
| ***C12N 15/00*** | (2006.01) |

(52) U.S. Cl.
USPC ......... 422/28; 424/94.4; 435/183; 435/252.3; 435/320.1

(58) Field of Classification Search
None
See application file for complete search history.

(56) References Cited

U.S. PATENT DOCUMENTS

| | | | | |
|---|---|---|---|---|
| 4,842,758 | A | 6/1989 | Crutzen | |
| 5,256,557 | A | 10/1993 | Shetty et al. | |
| 5,306,352 | A | 4/1994 | Nicolson et al. | |
| 5,549,891 | A | 8/1996 | Sulc et al. | |
| 5,549,894 | A | 8/1996 | Hunt | |
| 5,904,736 | A | 5/1999 | Maurer et al. | |
| 6,030,933 | A | 2/2000 | Herbots et al. | |
| 6,036,918 | A | 3/2000 | Kowanko | |
| 6,432,661 | B1 | 8/2002 | Heitfeld et al. | |
| 6,514,927 | B2 | 2/2003 | Lang et al. | |
| 6,627,657 | B1 | 9/2003 | Hilgren et al. | |
| 6,835,703 | B1 | 12/2004 | Cho et al. | |
| 6,949,178 | B2 | 9/2005 | Tennakoon et al. | |
| 7,098,179 | B2 | 8/2006 | Penninger et al. | |
| 7,316,995 | B2 | 1/2008 | Penninger | |
| 8,226,939 | B2 * | 7/2012 | Herdt et al. | 424/94.4 |
| 8,231,917 | B2 * | 7/2012 | Herdt et al. | 426/323 |
| 8,241,624 | B2 * | 8/2012 | Herdt et al. | 424/94.4 |
| 2004/0009474 | A1 | 1/2004 | Leach et al. | |
| 2005/0239681 | A1 | 10/2005 | Speckmann et al. | |
| 2007/0042924 | A1 | 2/2007 | Dicosimo et al. | |
| 2007/0098751 | A1 | 5/2007 | Hilgren et al. | |
| 2007/0280919 | A1 | 12/2007 | Gorton | |

FOREIGN PATENT DOCUMENTS

| | | |
|---|---|---|
| EP | 0223479 | 5/1987 |
| EP | 274946 | 4/1992 |
| EP | 549048 | 4/2000 |
| EP | 1375634 | 1/2004 |
| WO | WO2007/148410 | 12/2007 |

OTHER PUBLICATIONS

International Search Report and Written Opinion mailed Oct. 29, 2009.

* cited by examiner

*Primary Examiner* — Christian Fronda
(74) *Attorney, Agent, or Firm* — Merchant & Gould PC

(57) ABSTRACT

The present invention relates to specially selected catalase enzymes and their use in reducing hydrogen peroxide in applications, and particularly in aseptic packaging applications.

18 Claims, 1 Drawing Sheet

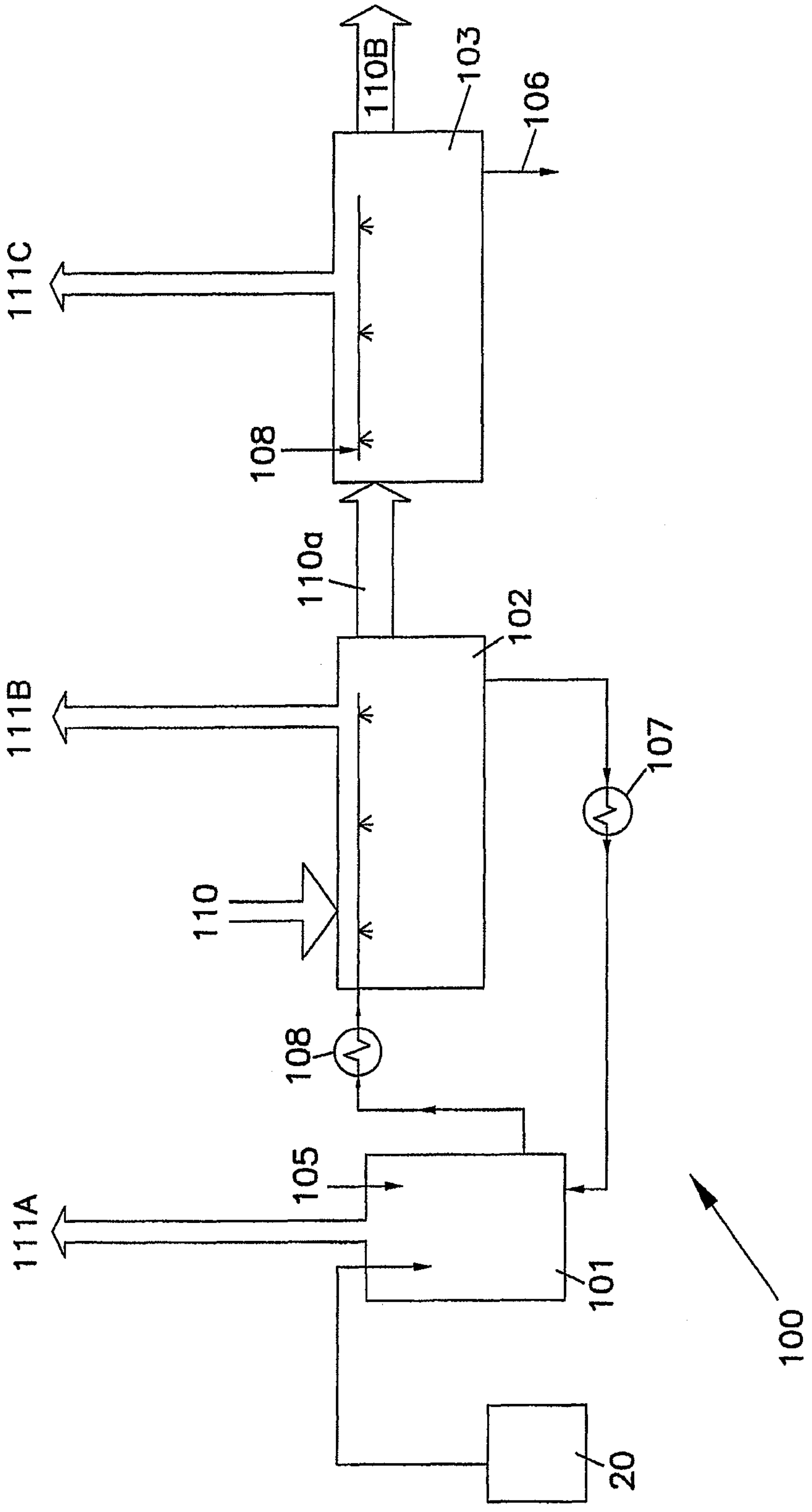
110B
103
106
111C
108
110a
102
111B
107
110
108
105
111A
101
100
20

METHODS OF DISINFECTING PACKAGES IN ASEPTIC PACKAGING USING ANTIMICROBIAL PERACID COMPOSITIONS WITH SELECTED CATALASE ENZYMES

CROSS REFERENCE TO RELATED APPLICATIONS

This application is a continuation of U.S. application Ser. No. 12/185,200 filed Aug. 4, 2008, issued as U.S. Pat. No. 8,226,939 on Jul. 24, 2012, which claims benefit to U.S. Provisional Application Serial No. 61/046,232 filed Apr. 18, 2008, both of which are incorporated herein by reference in their entirety.

FIELD OF THE INVENTION

The present invention relates to specially selected catalase enzymes and their use in reducing hydrogen peroxide in peracid antimicrobial composition in industrial applications, and particularly in aseptic packaging applications.

BACKGROUND

In the food, beverage and dairy market there exists a wide array of shelf stable packaged liquid and semi-liquid foods. These range from canned soups, to highly acidified soda and sport drinks.

Until 30 years ago the only options available for production of a shelf stable food with low acidity was thermal sterilization of both the packing and the food in a unitized manner. This was done either through pressure cooking, processing of sealed containers, or by filling thermally resistant packaging with a hot liquid food (the heat of the liquid food thereby sterilizing the packaging).

The introduction of aseptic packaging called for thermal sterilization of a liquid food stuff and separate chemical sterilization of the food packaging. This allowed for shorter thermal treatment of the food and the processing of foods that would have normally not been suitable for shelf stable food processing.

A chemical sterilant used in aseptic packaging is peracid. Peracid exists in equilibrium with its corresponding carboxylic acid and hydrogen peroxide. The equilibrium shifts to the reactant side or the product side of the chemical equilibrium equation based on the concentration of reactants or products present in a given solution.

Normally a peracid is provided to an end-user as an equilibrium concentrate and the end-user dilutes the concentrate to the level that is required for microbial treatment of their surface of interest. Over time, the peracid inside a sump in aseptic packaging operation slowly degrades or equilibrates back to the carboxylic acid and hydrogen peroxide. As a result, the sump accumulates higher levels of hydrogen peroxide and carboxylic acid. Filler manufacturers and customers have specifications set for maximum levels of hydrogen peroxide or carboxylic acid in the sump. When the sump approaches this limit it can be shut down, drained and refilled with fresh solution. Other filler manufactures will set the system up so that it has a certain bleed off rate. Adjusting the bleed off rate will modify the accumulation rate of peroxide and carboxylic acid in the sump so that the line can be run for an extended length of time. Both of these procedures increase the amount of water, energy, and chemistry required to operate an aseptic filler. It is against this background that the present invention has been made.

SUMMARY

Surprisingly, it has been discovered that selected catalase enzymes are particularly effective at decomposing hydrogen peroxide under the temperature and pH conditions found in peracid compositions and in particular in peracid compositions that are used in aseptic packaging.

The use of the selected catalase enzymes degrades hydrogen peroxide in aseptic filling operations which leads to decreased water, chemistry, and energy consumption because the system has to be drained less often. Accordingly, this invention relates to a method of disinfecting packages using aseptic packaging by providing a peracid antimicrobial composition comprising selected catalase enzymes, hydrogen peroxide, carboxylic acid, and percarboxylic acid, heating the antimicrobial compositions and applying the antimicrobial composition to a surface of a food package in an amount that renders the final food product located in the food package suitable for distribution and sale under nonrefrigerated storage conditions. This invention also relates to a method of disinfecting packages using aseptic packaging by providing an antimicrobial composition that has selected catalase enzymes, hydrogen peroxide, a carboxylic acid selected from the group consisting of acetic acid, octanoic acid and mixtures thereof and a peracid selected from the group consisting of peracetic acid, peroctanoic acid and mixtures thereof, heating the antimicrobial composition and applying the antimicrobial composition to a surface of a food package in an amount sufficient to render the final food product located in the food package suitable for distribution and sale under nonrefrigerated storage conditions.

This invention also relates to a method of disinfecting packages using aseptic packaging by forming an antimicrobial composition in a sump, heating the composition in the sump and pumping a portion of the antimicrobial composition from this sump to the package and applying the composition to the surface of a food package in an amount sufficient to render the final food product located in the food package suitable for distribution and sale under nonrefrigerated storage conditions, while simultaneously monitoring the concentration of hydrogen peroxide in the sump and adding additional catalase enzyme into the sump to maintain the concentration of hydrogen peroxide below a certain threshold.

These and other embodiments will be apparent to those of skill in the art and others in view of the following detailed description of some embodiments. It should be understood, however, that this summary, and the detailed description illustrate only some examples of various embodiments, and are not intended to be limiting to the invention as claimed.

BRIEF DESCRIPTION OF THE DRAWINGS

FIG. 1 shows a schematic of a bottling operation.

DETAILED DESCRIPTION OF SOME EMBODIMENTS

As discussed above, the invention generally relates to the use of selected catalase enzymes in peracid compositions and in particular in peracid compositions that are used in aseptic packaging.

Catalase Enzyme

The present invention uses a catalase enzyme to reduce the concentration of hydrogen peroxide in the antimicrobial composition. Catalase enzymes catalyze the decomposition of hydrogen peroxide to water and oxygen. Sources of catalase enzymes include animal sources such as bovine catalase isolated from beef livers, fungal catalases isolated from fungi including *Penicillium chrysogenum, Penicillium notatum*, and *Aspergillus niger*, plant sources, bacterial sources such as *Staphylococcus aureus*, and genetic variations and modifications thereof. Surprisingly, it has been found that fungal catalases are especially suited for use in peracid antimicrobial compositions and the resulting composition is useful in applications such as aseptic packaging. The preferred catalases are desirable because of their ability to decompose hydrogen peroxide at lower concentrations of catalase enzyme compared to non-fungal catalase enzymes. Additionally, the fungal catalase enzymes are more stable in the pH, temperature, and acidity environment found in peracid compositions and aseptic packaging operations.

Catalase enzymes used in this invention include catalase enzymes with a high ability to decompose hydrogen peroxide. In some embodiments, the catalase enzyme is able to degrade at least about 500 ppm of hydrogen peroxide in a peracid composition in 15 minutes.

Catalase enzymes used in this invention include catalase enzymes with a high ability to decompose hydrogen peroxide at low concentrations of catalase enzymes. In some embodiments, the concentration of catalase enzyme needed to degrade 500 ppm of hydrogen peroxide in a peracid composition in 15 minutes is less than 200 ppm, less than 100 ppm, and less than 50 ppm.

Catalase enzymes used in this invention include catalase enzymes with a tolerance to temperature ranges found in aseptic packaging applications. Typical aseptic operating temperatures can range from 40-65° C. A suitable enzyme should be able to maintain at least 50% of it activity under storage @ 65° C. for 1 hour.

Catalase enzymes used in this invention include catalase enzymes with a tolerance to pH ranges found in aseptic packaging applications. The acetic acid level in an aseptic packaging operation can reach 20000 ppm in the sump. This produces a solution in a pH range of about 2.0-2.5. A suitable enzyme maintains 50% of its activity under storage of a solution containing about 20000 ppm acetic acid over a period of one hour.

The catalase may be free floating in the antimicrobial composition, meaning that the catalase enzyme is part of the antimicrobial composition without being bound to a surface.

Alternatively, the catalase may be immobilized on a surface that is in fluid communication with the antimicrobial composition in way that allows the catalase to interact with and decompose hydrogen peroxide. Immobilized catalase may be more stable than unbound, soluble enzyme. Immobilized catalase also shows increased thermal and pH stability which might be due to the protection the substrate provides against sudden thermal and pH changes. An immobilized catalase also has the advantage of being able to be removed from the rest of the composition easily. An immobilized catalase may include a soluble catalase that is attached to a substrate. Examples of substrates may include polyurethane foams, polyacrylamide gels, polyethylenemaleic anhydride gels, polystyrenemaleic anhydride gels, cellulose, nitrocellulose, silastic resins, porous glass, macroporous glass membranes, glass beads, activated clay, zeolites, alumina, silica, silicate and other inorganic and organic substrates. The enzyme may be attached to the substrate in various ways including carrier covalent binding, crosslinking, physical adsorption, ionic binding, and entrapping.

Commercially available catalases are available in liquid and spray dried forms. Commercially available catalase includes both the active enzyme as well as additional ingredients to enhance the stability of the enzyme. Some exemplary commercially available catalase enzymes include Genencor CA-100 and CA-400 as well as Mitsubishi Gas and Chemical (MGC) ASC super G and ASC super 200.

The invention preferably includes at least one fungal catalase. Preferred commercially available fungal catalase enzymes include Genencor CA-400 and MGC ASC super 200.

Hydrogen Peroxide

The composition includes hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid.

Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and compatible with food products (e.g., does not substantially alter the color, flavor, or nutritional value of a food product). And the decomposition products are generally innocuous to incidental contact with humans and are environmentally friendly.

A composition of the invention typically includes hydrogen peroxide in an amount effective for maintaining the equilibrium between a carboxylic acid, hydrogen peroxide, and a peracid. The amount of hydrogen peroxide should not exceed an amount that would adversely affect the antimicrobial activity of a composition of the invention. Moreover, a composition of the invention preferably contains hydrogen peroxide at a concentration as close to zero as possible. That is, the concentration of hydrogen peroxide is minimized, particularly through the use of the selected catalase enzymes.

One advantage of minimizing the concentration of hydrogen peroxide is that antimicrobial activity of a composition of the invention is improved as compared to conventional compositions. Also it increases the run time when peracid compositions are used in aseptic packaging operations because the composition needs to be drained and refreshed less often.

Hydrogen peroxide can typically be present in a use solution in an amount of up to about 2500 ppm, preferably between about 3 ppm and about 1850 ppm, and more preferably between about 6 ppm and about 1250 ppm.

Carboxylic Acid

A composition of the invention also includes a carboxylic acid. A carboxylic acid includes any compound of the formula R—$(COOH)_n$ in which R can be hydrogen, alkyl, alkenyl, alicyclic group, aryl, heteroaryl, or heterocylic group, and n is 1, 2, or 3. Preferably R includes hydrogen, alkyl, or alkenyl.

The term "alkyl" includes a straight or branched saturated aliphatic hydrocarbon chain having from 1 to 12 carbon atoms, such as, for example, methyl, ethyl, propyl, isopropyl (1-methylethyl), butyl, tert-butyl (1,1-dimethylethyl), and the like.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like.

The above alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

The term "alicyclic" includes any cyclic hydrocarbyl containing from 3 to 8 carbon atoms. Examples of suitable alicyclic groups include cyclopropanyl, cyclobutanyl, cyclopentanyl, etc.

The term "heterocyclic" includes any cyclic hydrocarbyl containing from 3 to 8 carbon atoms that is interrupted by a heteroatom, such as, for example, a nitrogen, sulfur, or oxygen atom. Examples of suitable heterocyclic groups include groups derived form tetrahydrofurans, furans, thiophenes, pyrrolidines, piperidines, pyridines, pyrrols, picoline, coumaline, etc.

Alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, $SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy.

The term "aryl" includes aromatic hydrocarbyl, including fused aromatic rings, such as, for example, phenyl and naphthyl.

The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc.

The term "heteroaryl" also includes fused rings in which at least one ring is aromatic, such as, for example, indolyl, purinyl, benzofuryl, etc.

Aryl and heteroaryl groups can be unsubstituted or substituted on the ring by, for example, aryl, heteroaryl, alkyl, alkenyl, alkoxy, amino, carboxy, halo, nitro, cyano, $—SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Examples of suitable carboxylic acids include a variety monocarboxylic acids, dicarboxylic acids, and tricarboxylic acids.

Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc.

Dicarboxylic acids include, for example, adipic acid, fumaric acid, glutaric acid, maleic acid, succinic acid, malic acid, tartaric acid, etc.

Tricarboxylic acids include, for example, citric acid, trimellitic acid, isocitric acid, agaicic acid, etc.

A carboxylic acid suitable for use in a composition of the invention can be selected for its solubility, cost, approval as food additive, odor, purity, etc.

A particularly useful carboxylic acid for a composition of the invention includes a carboxylic acid that is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. These carboxylic acids can also be useful because water-soluble carboxylic acids can be food additives such as formic acid, acetic acid, lactic acid, citric acid, tartaric acid, etc.

Preferably a composition of the invention includes acetic acid, octanoic acid, or propionic acid, lactic acid, heptanoic acid, octanoic acid, or nonanoic acid.

A composition of the invention can include a carboxylic acid in an amount that can be effectively removed from the inside and outside of a package in an aseptic filler during the rinsing step of the aseptic packaging process. A carboxylic acid can typically be present in a use solution in an amount less than 40000 ppm, preferably less than 30000 ppm and more preferably less than 20000 ppm.

Peracid

A composition of the invention also includes a peracid. A peracid is also known in the art as a percarboxylic acid, a peroxyacid, and a peroxycarboxylic acid.

A peracid includes any compound of the formula $R—(COOOH)_n$ in which R can be hydrogen, alkyl, alkenyl, alicyclic group, aryl, heteroaryl, or heterocyclic group, and n is 1, 2, or 3. Preferably R includes hydrogen, alkyl, or alkenyl.

The terms "alkyl," "alkenyl," "alicyclic group," "aryl," "heteroaryl," and "heterocyclic group" are as defined above.

Peracids used in this invention include any peroxycarboxylic acid that can be prepared from the acid-catalyzed equilibrium reaction between a carboxylic acid described above and hydrogen peroxide described above. Preferably a composition of the invention includes peroxyacetic acid, peroxyoctanoic acid, or peroxypropionic acid, peroxylactic acid, peroxyheptanoic acid, peroxyoctanoic acid, or peroxynonanoic acid.

A peroxycarboxylic acid can also be prepared by the autooxidation of aldehydes or by the reaction of hydrogen peroxide with an acid chloride, acid hydride, carboxylic acid anhydride, or sodium alcoholate.

In some embodiments, a peroxycarboxylic acid includes at least one water-soluble peroxycarboxylic acid in which R includes alkyl of 1-4 carbon atoms. For example, in one embodiment, a peroxycarboxylic acid includes peroxyacetic acid. In another embodiment, a peroxycarboxylic acid has R that is an alkyl of 1-4 carbon atoms substituted with hydroxy.

Methods of preparing peroxyacetic acid are known to those of skill in the art including those disclosed in U.S. Pat. No. 2,833,813, which is incorporated herein by reference.

One advantage of using a peroxycarboxylic acid in which R includes alkyl of 1-4 carbon atoms is that such peroxycarboxylic acids traditionally have a lower pKa than peroxycarboxylic acids having R that is alkyl with more than 4 carbon atoms. This lower pKa can favor a faster rate of peroxycarboxylic acid equilibrium and can be effective for providing a composition of the invention with, for example, acidic pH, which can be advantageous for improved lime-scale and/or soil removal.

In other embodiments, a peroxycarboxylic acid includes at least one peroxycarboxylic acid of limited water solubility in which R includes alkyl of 5-12 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid.

One advantage of combining a water-soluble carboxylic acid or peroxycarboxylic acid with a carboxylic acid or peroxycarboxylic acid having limited water solubility is that the water-soluble carboxylic acid or peroxycarboxylic acid can provide a hydrotropic effect upon less water soluble carboxylic and peroxycarboxylic acids, which can facilitate uniform dispersion and/or consequent physical stability within the composition.

Another advantage of this combination of peroxycarboxylic acids is that it can provide a composition of the invention with desirable antimicrobial activity in the presence of high organic soil loads.

A composition of the invention can include a peroxycarboxylic acid, or mixtures thereof, in an amount effective for the sterilization of bacterial and fungal spores of public health and spoilage significance on the inside and outside surfaces of a food package in an aseptic filler as well as within the enclosure of the filler itself. A peroxycarboxylic acid can typically be present in this composition in an amount of between about 500 ppm and about 6000 ppm, preferably between about 1000 ppm and 5000 ppm, and more preferably between about 1500 ppm and about 4000 ppm.

Additional Optional Materials

The composition can optionally include additional ingredients to enhance the composition including stabilizing agents, hydrotropes, surfactants, defoamers, corrosion inhibitors, rheology modifiers, dyes, and fragrances.

Stabilizing Agents

The composition may optionally include stabilizing agents to stabilize the peracid and hydrogen peroxide and prevent the premature oxidation of this constituent within the composition.

Chelating agents or sequestrants generally useful as stabilizing agents in the present compositions include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelating agents include nitroloacetates and their derivatives, and mixtures thereof. Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA); N-hydroxyethyl-ethylenediaminetriacetic acid (HEDTA); tetrasodium ethylenediaminetetraacetic acid (EDTA); diethylenetriaminepentaacetic acid (DTPA); and alanine-N,N-diacetic acid; n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms. Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelating agents include polyaspartic acid or co-condensates of aspartic acid with other amino acids, $C_4$-$C_{25}$-mono- or -dicarboxylic acids and $C_4$-$C_{25}$-mono- or -diamines. Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

The chelating agent may be present in an amount from about 0.01 to about 5 wt. %, from about 0.05 to about 3 wt. %, and from about 0.1 to about 1.5 wt. %.

Hydrotropes

The composition may optionally include a hydrotrope coupler or solubilizer. Such materials can be used to ensure that the composition remains phase stable and in a single highly active aqueous form. Such hydrotrope solubilizers or couplers can be used at concentrations that maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Coupling agents can also include n-octane sulfonate, aromatic sulfonates such as an alkyl aryl sulfonate (e.g., sodium xylene sulfonate or naphthalene sulfonate), and alkylated diphenyl oxide disulfonic acids, such as those sold under the DOWFAX™ trade name, preferably the acid forms of these hydrotropes.

The concentration of hydrotrope useful in the present invention generally ranges from about 0.1 to about 20 wt-%, preferably from about 2 to about 18 wt-%, most preferably from about 3 to about 15 wt-%.

Surfactants

The composition may optionally include a surfactant or mixture of surfactants. The surfactant may include anionic, nonionic, cationic, and zwitterionic surfactants, which are commercially available, and mixtures thereof. In an embodiment, the surfactant includes a nonionic or anionic surfactant. For a discussion of surfactants, see Kirk-Othmer, *Encyclopedia of Chemical Technology*, Third Edition, volume 8, pages 900-912.

Nonionic surfactants can include those having a polyalkylene oxide polymer as a portion of the surfactant molecule. These surfactants can be capped or uncapped. Such nonionic surfactants include, for example, chlorine-, benzyl-, methyl-, ethyl-, propyl-, butyl- and other like alkyl-capped polyethylene glycol ethers of fatty alcohols; polyalkylene oxide free nonionics such as alkyl polyglycosides; sorbitan and sucrose esters and their ethoxylates; alkoxylated ethylene diamine; alcohol alkoxylates such as alcohol ethoxylate propoxylates, alcohol propoxylates, alcohol propoxylate ethoxylate propoxylates, alcohol ethoxylate butoxylates, fatty alcohol ethoxylates (e.g., tridecyl alcohol alkoxylate, ethylene oxide adduct), and the like; nonylphenol ethoxylate, polyoxyethylene glycol ethers, and the like; carboxylic acid esters such as glycerol esters, polyoxyethylene esters, ethoxylated and glycol esters of fatty acids, and the like; carboxylic amides such as diethanolamine condensates, monoalkanolamine condensates, polyoxyethylene fatty acid amides, and the like; and polyalkylene oxide block copolymers including an ethylene oxide/propylene oxide block copolymer such as those commercially available under the trademark PLURONIC (BASF-Wyandotte), and the like; ethoxylated amines and ether amines commercially available from Tomah Corporation and other like nonionic compounds. Silicone surfactants such as the ABIL B8852 (Goldschmidt) can also be used.

The nonionic surfactant can include linear and secondary alcohol ethoxylates (fatty alcohol ethoxylates, e.g., tridecyl alcohol alkoxylate, ethylene oxide adduct), alkyl phenol ethoxylates, ethoxy/propoxy block surfactants, and the like. Examples of preferred linear and secondary alcohol ethoxylates (fatty alcohol ethoxylates, e.g., tridecyl alcohol alkoxylate, ethylene oxide adduct) include five mole ethoxylate of linear, primary 12-14 carbon number alcohol ($C_{12-14}H_{25-29}$)—O—($CH_2CH_2O$)$_5$H (one of which is sold under the tradename LAE 24-5), seven mole ethoxylate of linear, primary 12-14 carbon number alcohol ($C_{12-14}H_{25-29}$)—O—($CH_2CH_2O$)$_{12}$H (one of which is sold under the tradename LAE 24-7), twelve mole ethoxylate of linear, primary 12-14 carbon number alcohol ($C_{12-14}H_{25-29}$)—O—($CH_2CH_2O$)$_{12}$H (one of which is sold under the tradename LAE 24-12), and the like.

Anionic surfactants can include, for example, carboxylates such as alkylcarboxylates (carboxylic acid salts) and polyalkoxycarboxylates, alcohol ethoxylate carboxylates, nonylphenol ethoxylate carboxylates, and the like; sulfonates such as alkylsulfonates, alkylbenzenesulfonates (e.g., linear dodecyl benzene sulfonic acid or salts thereof), alkylarylsulfonates, sulfonated fatty acid esters, and the like; sulfates such as sulfated alcohols, sulfated alcohol ethoxylates, sulfated alkylphenols, alkylsulfates, sulfosuccinates, alkylether sulfates, and the like; and phosphate esters such as alkylphosphate esters, ethoxylated alcohol phosphate esters, and the like. Preferred anionics include sodium alkylarylsulfonate, alkylbenzenesulfonates (e.g., linear dodecyl benzene sulfonic acid or salts thereof), and the like.

Surface active substances are classified as cationic if the charge on the hydrophilic portion of the molecule is positive. Surfactants in which the hydrophile carries no charge unless the pH is lowered close to neutrality or lower, but which are then cationic (e.g. alkyl amines), are also included in this group.

Cationic surfactants can include compounds containing at least one long carbon chain hydrophobic group and at least one positively charged nitrogen. The long carbon chain group may be attached directly to the nitrogen atom by simple substitution; or indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The cationic surfactant can include a quaternary ammonium surfactant, such as tallow quaternary ammonium surfactant, such as a tallow amine ethoxylate quaternary ammonium compound. For example, a tallow amine ethoxylate quaternary ammonium compound can include a quaternary nitrogen bonded to a methyl group, a tallow moiety, and two ethoxylate moieties. The ethoxylate moieties can include 6-10 ethoxylate groups. In an embodiment, the present composition can include about 1 to about 10 wt-% or about 5 wt-% of such a cationic surfactant.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The majority of large volume commercial cationic surfactants can be subdivided into four major classes and additional sub-groups, for example, as described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, dialkylammonium salts, and the like. Cationic surfactants are known to have a variety of properties that can be beneficial in the present compositions. These desirable properties can include detergency, antimicrobial efficacy, and the like.

Defoamers

The composition may optionally include defoamers. Generally, defoamers can include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; and phosphates and phosphate esters such as alkyl and alkaline diphosphates, and tributyl phosphates among others; and mixtures thereof. Food grade defoamers are preferred. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

Corrosion Inhibitors

The composition may optionally include a corrosion inhibitor. Useful corrosion inhibitors include polycarboxylic acids such as short chain carboxylic diacids, triacids, as well as phosphate esters and combinations thereof. Useful phosphate esters include alkyl phosphate esters, monoalkyl aryl phosphate esters, dialkyl aryl phosphate esters, trialkyl aryl phosphate esters, and mixtures thereof such as Emphos PS 236 commercially available from Witco Chemical Company. Other useful corrosion inhibitors include the triazoles, such as benzotriazole, tolyltriazole and mercaptobenzothiazole, and in combinations with phosphonates such as 1-hydroxyethylidene-1,1-diphosphonic acid, and surfactants such as oleic acid diethanolamide and sodium cocoamphohydroxy propyl sulfonate, and the like. Useful corrosion inhibitors include polycarboxylic acids such as dicarboxylic acids. The acids which are preferred include adipic, glutaric, succinic, and mixtures thereof. The most preferred is a mixture of adipic, glutaric and succinic acid, which is a raw material sold by BASF under the name SOKALAN® DCS.

Rheology Modifiers

A composition may optionally include one or more rheology modifiers.

Water soluble or water dispersible rheology modifiers that are useful can be classified as inorganic or organic. The organic thickeners can further be divided into natural and synthetic polymers with the latter still further subdivided into synthetic natural-based and synthetic petroleum-based.

Inorganic thickeners are generally compounds such as colloidal magnesium aluminum silicate (VEEGUM®), colloidal clays (Bentonites), or silicas (CAB-O-SILS®) which have been fumed or precipitated to create particles with large surface to size ratios. Suitable natural hydrogel thickeners are primarily vegetable derived exudates. For example, tragacanth, karaya, and acacia gums; and extractives such as carrageenan, locust bean gum, guar gum and pectin; or, pure culture fermentation products such as xanthan gum. Chemically, all of these materials are salts of complex anionic polysaccharides. Synthetic natural-based thickeners having application are cellulose derivatives wherein the free hydroxyl groups on the linear anhydro-glucose polymers have been etherified or esterified to give a family of substances, which dissolve in water and give viscous solutions. This group of materials includes the alkyl and hydroxyllalkycelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

Dyes and Fragrances

The composition may optionally include various dyes, odorants including perfumes, and other aesthetic enhancing agents. Preferred dyes include FD&C dyes, D&C dyes, and the like.

Use in Aseptic Packaging

Aseptic packaging fillers can be broken down into two basic categories: a single use filler and a re-use or recirculating filler.

The single use system makes a dilute stock solution of peracid. It sprays a small amount of this solution in the inside of a package to sterilize it. The solution can be heated at the point of injection or it can be pre-heated prior to injection into the bottle. In either case the running conditions (temperature, contact time, and peracid concentration) are chosen so that the bottle is rendered commercially sterile. After contacting in the inside of the bottle, this spent solution drains from the bottle and is exported by the filler either to a drain or to other parts of the machine for environmental antimicrobial treatments or treatment of the exterior of the bottles.

After the bottle has been treated it will be rinsed with microbially pure water, filled with a liquid food and sealed. All of these steps occur inside of a positive pressure zone inside the filler called the sterile zone.

In a re-use filler, the filler contains a sump of diluted peracid solution. This sump is held at the desired temperature (40-65° C.). The filler draws from this sump and uses the solution to sterilize both the inside and outside of the bottles. The solution drains away from the bottles and it is collected and exported back to the same sump from which it originated.

After the bottle has been treated it will be rinsed with microbiologically pure water, filled with a liquid food and sealed. All of these steps occur inside of a positive pressure zone inside the filler called a sterile zone.

Aseptic packaging includes contacting the container with a composition according to the present invention. Such contacting can be accomplished using a spray device or soaking tank or vessel to intimately contact the inside of the container with the composition for sufficient period of time to clean or reduce the microbial population in the container. The container is then emptied of the amount of the present composition used. After emptying, the container can then be rinsed with potable water or sterilized water (which can include a rinse additive) and again emptied. After rinsing, the container can be filled with the food. The container is then sealed, capped or closed and then packed for shipment for ultimate sale.

Examples of containers that can be filled include polyethylene terephthalate (PET), high density polyethylene (HDPE), polypropylene (PP), low density polyethylene, polycarbonate (PC), poly vinyl alcohol (PVA), aluminum, single or multilayer films or pouches, paperboard, steel, glass, multilayer bottles, other polymeric packaging material, combinations of these materials in films, pouches, bottle, or other food packaging materials.

During operation the enzyme can be added in bulk or in sequence. The enzyme may be free floating or immobilized on a substrate. The enzyme can be added to the peracid in the sump. Also the enzyme is preferably added at the point of use and not added before shipping the product.

FIG. 1 shows a schematic for an embodiment of a bottle spraying/bottling operation using a composition according to the present invention. The operation can be a cold aseptic operation. FIG. 1 shows a plant 100 that can contact beverage bottles with a peroxycarboxylic acid composition for a sanitizing regime. In FIG. 1, bottles 110 are passed through a sterilizing tunnel 102. The sanitized bottles 110*a* then pass through a rinsing tunnel 103 and emerge as sanitized rinsed bottles 110*b*.

In the process, the composition is added to a holding tank 101. Commonly, the materials are maintained at a temperature of about 22° C. in tank 101. The peroxycarboxylic acid use composition is passed through a heater 108 to reach a temperature of about 40-65° C. The heated peroxycarboxylic acid use composition is sprayed within sterilizing tunnel 102 into and onto all surfaces of the bottle 110. The composition may be pumped from the holding tank or sump to the bottle at a rate of about 0.01-5.0 liters per second.

After contact with the peroxycarboxylic acid use composition and after dumping any excess composition from the bottles, the sanitized bottles 110 are then passed to a fresh water rinse tunnel 103. Fresh water 108 is provided from a fresh water make-up into a spray rinsing tunnel 103. The fresh water can include a rinse additive. Excess spray drains from rinsing tunnel 103 to drain 106. Within the tunnel 103, sanitized bottles 110*a* are thoroughly rinsed with fresh water. The complete removal of the peroxycarboxylic acid composition from the bottles 110*a* is important for maintaining high quality of the beverage product. The rinsed and sanitized bottles 110*b* are then removed from the rinsing tunnel.

The day tank 101, the sterilizing tunnel 102 and the rinsing tunnel 103 are all respectively vented to wet scrubber or vent 111*a*, 111*b* or 111*c* to remove vapor or fumes from the system components. The sanitizer material that has been sprayed and drained from the bottles 110*a* accumulate in the bottom of the spray tunnel 102 and is then optionally recycled through recycle line and heater 107 into the day tank 101, out of the system to the drain, or for use or exported in another part of the plant.

The contact between the bottles and the peroxycarboxylic acid antimicrobial composition can be at a temperature of greater than about 0° C., greater than 25° C., or greater than about 40° C. Temperatures between about 40° C. and 90° C. can be used. In certain embodiments, contact at 40° C. to 60° C. for at least 5 sec, or at least about 10 sec, is employed.

In the cold aseptic filling of 16 ounce polyethylene terephthalate (PET bottle), or other polymeric, beverage containers, a process has been adopted using a peroxycarboxylic acid composition. The peroxycarboxylic acid composition can be diluted to a use concentration of about 0.1 to about 10 wt % and maintained at an effective elevated temperature of about 25° C. to about 70° C., e.g., about 40° C. to about 60° C. The spray or flood of the bottle with the material ensures contact between the bottle and the sanitizer material for at least 5, e.g., about 10, seconds, up to 2 minutes. After flooding is complete, the bottle can be drained of all contents for a minimum of 2 seconds and optionally followed by a 5 second water rinse with sterilized water using about 200 milliliters of water at 38° C. (100° F.). If optionally filled with the rinse water, the bottle is then drained of the sterilized water rinse for at least 2 seconds and is immediately filled with liquid beverage. The rinse water can include a rinse additive which the selected catalase enzymes are especially useful in aseptic packaging, it is understood that they can be used anywhere peracid compositions are used where the catalase can be introduced into the peracid composition without having to store the peracid and catalase together. Such uses include peracid compositions in the healthcare, and food and beverage, warewashing, laundry and housekeeping industries.

For a more complete understanding of the invention, the following examples are given to illustrate some embodiment. These examples and experiments are to be understood as illustrative and not limiting. All parts are by weight, except where it is contrarily indicated.

EXAMPLES

The following chart provides a brief explanation of certain chemical components used in the following examples:

Trade Names and Corresponding Descriptions of Some Chemicals Used in the Examples

| Trademark/Chemical Name | Description | Provider |
|---|---|---|
| Bovine Catalase | crystaline bovine liver catalase | Sigma Aldrich |
| ASC Super G | biological catalase concentrate | Mitsubishi |
| ASC Super 200 | biological catalase concentrate | Mitsubishi |
| CA-100 | biological catalase concentrate | Genencor |
| CA-400 | biological catalase concentrate | Genencor |
| Hydrogen Peroxide | 35-50% $H_2O_2$ | Solvay-Interox Corp. |

Example 1

Example 1 compared the ability to various catalase enzymes at 100 ppm concentration to decompose hydrogen peroxide. For this example, an aliquot of a stock solution of catalase was added to 1000 ml of a solution containing about 20,000 ppm acetic acid and 500-800 ppm of hydrogen peroxide at 60° C. The catalase addition was done at a rate that produced an enzyme concentration of 100 ppm in the 1000 ml solution The concentration of the hydrogen peroxide was measured at time zero and at 5, 10, and 15 minutes. The concentration of hydrogen peroxide was measured via titration of a 10 ml aliquot of solution including 1-2 ml of 10.0 KI solution, 1-2 ml concentrated sulfuric acid, 4-5 drops of an oxygen catalyst (saturated solution of Ammonium Molybdate) and a few drops of a starch solution. The titrant was 0.1 N Sodium thiosulfate. The solution was titrated to a colorless endpoint and the peroxide concentration was calculated via the following calculation:

$$\text{ppm H2O2} = \frac{(\text{ml } Na_2S_2O_3)(\text{Normality of titration})(\text{Equivalent wt } H_2O_2)}{(\text{sample size})(2)}$$

$$\text{ppm H2O2} = \frac{(\text{ml } Na_2S_2O_3)(0.1)(34)}{(10\text{ g})(2)}$$

The concentration of hydrogen peroxide is shown in Table 1.

TABLE 1

Hydrogen Peroxide Concentration (ppm) Over Time (minutes) in the Presence of 100 ppm Catalase

| Time | Bovine | ASC Super G | ASC Super 200 | CA-100 | CA-400 |
|---|---|---|---|---|---|
| 0 | 581.4 | 688.5 | 595 | 765 | 739.5 |
| 5 | 564.4 | 76.5 | 8.5 | 246.5 | 8.5 |
| 10 | 561 | 0 | 0 | 85 | 0 |
| 15 | 552.5 | 0 | 0 | 42.5 | 0 |

Table 1 shows that the fungal catalases, including ASC Super G, ASC Super 200, and CA-400 in particular, were able to decrease the concentration of hydrogen peroxide to zero after 10 minutes. The bovine catalase only decreased the concentration of hydrogen peroxide by 28.9 ppm.

Example 2

Example 2 compared the ability to various catalase enzymes at 20 ppm concentration to decompose hydrogen peroxide. For this example, 20 ppm of catalase enzyme was diluted in 20,000 ppm acetic acid and 500-800 ppm of hydrogen peroxide at 60° C. The concentration of the hydrogen peroxide was measured at time zero and at 5, 10, and 15 minutes in the same manner as outlined in example 1. The concentration of hydrogen peroxide is shown in Table 2.

TABLE 2

Hydrogen Peroxide Concentration (ppm) Over Time (minutes) in the Presence of 20 ppm Catalase

| Time | Bovine | ASC Super G | ASC Super 200 | CA-100 | CA-400 |
|---|---|---|---|---|---|
| 0 | 600 | 680 | 578 | 765 | 731 |
| 5 | 600 | 493 | 102 | 425 | 323 |
| 10 | 600 | 493 | 25.5 | 340 | 136 |
| 15 | 600 | 493 | 8.5 | 306 | 59.5 |

Table 2 shows that the fungal catalases, and ASC Super G, ASC Super 200, and CA-400 in particular, were able to measurably decrease the concentration of hydrogen peroxide. The bovine catalase did not measurably decrease the concentration of hydrogen peroxide.

Example 3

Example 3 determined the temperature stability of the CA-400 catalase. For this example, a 5000 ppm sample of CA-400 was placed in a small glass vial and placed in a water bath at 60° C. Samples of the CA-400 were removed from the water bath and placed in an ice water bath after certain exposure times. After the ice water bath, the sample was tested against hydrogen peroxide at room temperature in a UV-VIS spectrophotometer at 240 nm for 2 minutes. A sample of the enzyme in distilled water was also run. The sample was prepared for the spectrophotometer by pipeting 3 ml of a stock solution of hydrogen peroxide into a 1 cm×1 cm quartz cuvette. 250 microliters of the catalase solution was added to the hydrogen peroxide solution. The spectrophotometer took measurements at 15 second intervals. The raw absorbance numbers are shown in Table 3. The adjusted absorbance numbers (raw catalase in hydrogen peroxide numbers—distilled water control) are shown in Table 4. The spectrophotometer measurements were converted into hydrogen peroxide concentration. The concentration of hydrogen peroxide was calculated via the following formulation:

$$\text{ppm } H_2O_2 = (\text{Abs } H_2O_2 \text{ with Enzyme solution} - \text{Abs Enzyme solution in water})(0.0012)(1000000)$$

The concentration of hydrogen peroxide (ppm) over time in shown in Table 5.

TABLE 3

| Spectrophotometer Measurements for CA-400 in Hydrogen Peroxide | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 0.9184 | 0.2875 | 0.1137 | 0.0944 | 0.05 | 0.05 | 0.05 | 0.05 |
| 0 hour | Sample 0b | 1.0063 | 0.2325 | 0.1391 | 0.11 | 0.073 | 0.05 | 0.05 | 0.05 |
| 1 hour | Sample 1a | 0.9836 | 0.2359 | 0.1714 | 0.1251 | 0.0792 | 0.05 | 0.05 | 0.05 |
| 1 hour | Sample 1b | 0.9723 | 0.3085 | 0.1734 | 0.0943 | 0.0832 | 0.05 | 0.05 | 0.05 |
| 2 hour | Sample 2a | 1.0342 | 0.3548 | 0.1957 | 0.1159 | 0.0879 | 0.05 | 0.05 | 0.05 |
| 2 hour | Sample 2b | 1.0184 | 0.3553 | 0.2219 | 0.1058 | 0.0879 | 0.05 | 0.05 | 0.05 |
| 4 hour | Sample 4a | 0.9956 | 0.2764 | 0.1966 | 0.0879 | 0.0725 | 0.05 | 0.05 | 0.05 |
| 4 hour | Sample 4b | 1.018 | 0.3032 | 0.1893 | 0.0828 | 0.0751 | 0.05 | 0.05 | 0.05 |
| Distilled Water Control | | | | | | | | | |
| 0 hour | | 0.05 | | | | | | | |
| 1 hour | | 0.05 | | | | | | | |
| 2 hour | | 0.05 | | | | | | | |
| 4 hour | | 0.05 | | | | | | | |

TABLE 4

| Adjusted Spectrophotometer Measurements for CA-400 | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 0.8684 | 0.2375 | 0.0637 | 0.0444 | 0 | 0 | 0 | 0 |
| 0 hour | Sample 0b | 0.9563 | 0.1825 | 0.0891 | 0.06 | 0.023 | 0 | 0 | 0 |
| 1 hour | Sample 1a | 0.9336 | 0.1859 | 0.1214 | 0.0751 | 0.0292 | 0 | 0 | 0 |
| 1 hour | Sample 1b | 0.9223 | 0.2585 | 0.1234 | 0.0443 | 0.0332 | 0 | 0 | 0 |
| 2 hour | Sample 2a | 0.9842 | 0.3048 | 0.1457 | 0.0659 | 0.0379 | 0 | 0 | 0 |
| 2 hour | Sample 2b | 0.9684 | 0.3053 | 0.1719 | 0.0558 | 0.0379 | 0 | 0 | 0 |
| 4 hour | Sample 4a | 0.9456 | 0.2264 | 0.1466 | 0.0379 | 0.0225 | 0 | 0 | 0 |
| 4 hour | Sample 4b | 0.968 | 0.2532 | 0.1393 | 0.0328 | 0.0251 | 0 | 0 | 0 |

TABLE 5

| Hydrogen Peroxide Concentration (ppm) with CA-400 Over Time | | | | | | | | | |
|---|---|---|---|---|---|---|---|---|---|
| | | Hydrogen Peroxide Concentration (ppm) Over Time (Seconds) | | | | | | | |
| Catalase Treatment | | 0 | 15 | 30 | 45 | 60 | 75 | 90 | 105 |
| 0 hour | Sample 0a | 1042.08 | 285 | 76.44 | 53.28 | 0 | 0 | 0 | 0 |
| 0 hour | Sample 0b | 1147.56 | 219 | 106.92 | 72 | 27.6 | 0 | 0 | 0 |
| average | | 1094.82 | 252 | 91.68 | 62.64 | 13.8 | 0 | 0 | 0 |
| 1 hour | Sample 1a | 1120.32 | 223.08 | 145.68 | 90.12 | 35.04 | 0 | 0 | 0 |
| 1 hour | Sample 1b | 1106.76 | 310.2 | 148.08 | 53.16 | 39.84 | 0 | 0 | 0 |
| average | | 1113.54 | 266.64 | 146.88 | 71.64 | 37.44 | 0 | 0 | 0 |
| 2 hour | Sample 2a | 1181.04 | 365.76 | 174.84 | 79.08 | 45.48 | 0 | 0 | 0 |
| 2 hour | Sample 2b | 1162.08 | 366.36 | 206.28 | 66.96 | 45.48 | 0 | 0 | 0 |
| average | | 1171.56 | 366.06 | 190.56 | 73.02 | 45.48 | 0 | 0 | 0 |
| 4 hour | Sample 4a | 1134.72 | 271.68 | 175.92 | 45.48 | 27 | 0 | 0 | 0 |
| 4 hour | Sample 4b | 1161.6 | 303.84 | 167.16 | 39.36 | 30.12 | 0 | 0 | 0 |
| average | | 1148.16 | 287.76 | 171.54 | 42.42 | 28.56 | 0 | 0 | 0 |
| Average Summary | | | | | | | | | |
| 0 hour | | 1094.82 | 252 | 91.68 | 62.64 | 13.8 | 0 | 0 | 0 |
| 1 hour | | 1113.54 | 266.64 | 146.88 | 71.64 | 37.44 | 0 | 0 | 0 |
| 2 hour | | 1171.56 | 366.06 | 190.56 | 73.02 | 45.48 | 0 | 0 | 0 |
| 4 hour | | 1148.16 | 287.76 | 171.54 | 42.42 | 28.56 | 0 | 0 | 0 |

Example 3 shows that CA-400 is stable at 60° C. over time because even after being in a hot water bath for four hours, it is still capable of decreasing the concentration of hydrogen peroxide to zero within 75 seconds.

Example 4

Example 4 determined the temperature stability of the CA-400 catalase in the presence of 20,000 ppm acetic acid. The enzyme was stored in the acetic acid for 0 to 1, 2 or 4 hours in the glass vial. For this example, a 5000 ppm sample of CA-400 along with 20000 ppm solution of acetic acid was in a small glass vial and placed in a water bath at 60° C. Samples of the CA-400 were removed from the water bath and placed in an ice water bath after certain exposure times. After the ice water bath, the sample was tested against hydrogen peroxide at room temperature in a UV-VIS spectrophotometer at 240 nm for 2 minutes. A sample of the enzyme in distilled water was also run. The sample was prepared for the spectrophotometer by pipeting 3 ml of a stock solution of hydrogen peroxide into a 1 cm×1 cm quartz cuvette. 250 microliters of the catalase solution was added to the hydrogen peroxide solution. The spectrophotometer took measurements at 15 second intervals. The raw numbers are shown in Table 6. The adjusted numbers (raw catalase in hydrogen peroxide numbers—distilled water control) are shown in Table 7. The spectrophotometer measurements were converted into hydrogen peroxide concentration. These values were calculated in the same manner as outlined in example 3. The concentration of hydrogen peroxide (ppm) over time in shown in Table 8.

TABLE 6

Spectrophotometer Measurements for CA-400 in Hydrogen Peroxide

| Catalase Treatment | | Spectrophotometer Measurements Over Time (Seconds) 0 | 15 | 30 | 45 | 60 | 75 | 90 | 105 |
|---|---|---|---|---|---|---|---|---|---|
| 0 hour | Sample 0a | 1.1666 | 0.6812 | 0.427 | 0.3128 | 0.2052 | 0.183 | 0.1047 | 0.1047 |
| 0 hour | Sample 0b | 1.1145 | 0.6276 | 0.42 | 0.3027 | 0.2442 | 0.1519 | 0.0933 | 0.0933 |
| 1 hour | Sample 1a | 1.0926 | 0.6724 | 0.4505 | 0.2843 | 0.2344 | 0.1524 | 0.1027 | 0.1057 |
| 1 hour | Sample 1b | 1.1337 | 0.6849 | 0.4448 | 0.2696 | 0.1908 | 0.1699 | 0.1049 | 0.1049 |
| 2 hour | Sample 2a | 1.1482 | 0.7066 | 0.4604 | 0.3438 | 0.2906 | 0.1409 | 0.1 | 0.1 |
| 2 hour | Sample 2b | 1.1284 | 0.6982 | 0.4516 | 0.2909 | 0.225 | 0.1453 | 0.1 | 0.1 |
| 4 hour | Sample 4a | 1.1613 | 0.7369 | 0.494 | 0.3115 | 0.2032 | 0.1746 | 0.1208 | 0.1208 |
| 4 hour | Sample 4b | 1.1437 | 0.6863 | 0.5325 | 0.3699 | 0.2462 | 0.2195 | 0.1218 | 0.1145 |
| Distilled Water Control | | | | | | | | | |
| 0 hour | | 0.05 | | | | | | | |
| 1 hour | | 0.05 | | | | | | | |
| 2 hour | | 0.05 | | | | | | | |
| 4 hour | | 0.05 | | | | | | | |

TABLE 7

Adjusted Spectrophotometer Measurements for CA-400

| Catalase Treatment | | Spectrophotometer Measurements Over Time (Seconds) 0 | 15 | 30 | 45 | 60 | 75 | 90 | 105 |
|---|---|---|---|---|---|---|---|---|---|
| 0 hour | Sample 0a | 1.1166 | 0.6312 | 0.377 | 0.2628 | 0.1552 | 0.133 | 0.0547 | 0.0547 |
| 0 hour | Sample 0b | 1.0645 | 0.5776 | 0.37 | 0.2527 | 0.1942 | 0.1019 | 0.0433 | 0.0433 |
| 1 hour | Sample 1a | 1.0426 | 0.6224 | 0.4005 | 0.2343 | 0.1844 | 0.1024 | 0.0527 | 0.0557 |
| 1 hour | Sample 1b | 1.0837 | 0.6349 | 0.3948 | 0.2196 | 0.1408 | 0.1199 | 0.0549 | 0.0549 |
| 2 hour | Sample 2a | 1.0982 | 0.6566 | 0.4104 | 0.2938 | 0.2406 | 0.0909 | 0.05 | 0.05 |
| 2 hour | Sample 2b | 1.0784 | 0.6482 | 0.4016 | 0.2409 | 0.175 | 0.0953 | 0.05 | 0.05 |
| 4 hour | Sample 4a | 1.1113 | 0.6869 | 0.444 | 0.2615 | 0.1532 | 0.1246 | 0.0708 | 0.0708 |
| 4 hour | Sample 4b | 1.0937 | 0.6363 | 0.4825 | 0.3199 | 0.1962 | 0.1695 | 0.0718 | 0.0645 |

TABLE 8

Hydrogen Peroxide Concentration (ppm) with CA-400 Over Time

| Catalase Treatment | | Hydrogen Peroxide Concentration (ppm) Over Time (Seconds) 0 | 15 | 30 | 45 | 60 | 75 | 90 | 105 |
|---|---|---|---|---|---|---|---|---|---|
| 0 hour | Sample 0a | 1339.92 | 757.44 | 452.4 | 315.36 | 186.24 | 159.6 | 65.64 | 65.64 |
| 0 hour | Sample 0b | 1277.4 | 693.12 | 444 | 303.24 | 233.04 | 122.28 | 51.96 | 51.96 |
| average | | 1308.66 | 725.28 | 448.2 | 309.3 | 209.64 | 140.94 | 58.8 | 58.8 |
| 1 hour | Sample 1a | 1251.12 | 746.88 | 480.6 | 281.16 | 221.28 | 122.88 | 63.24 | 66.84 |
| 1 hour | Sample 1b | 1300.44 | 761.88 | 473.76 | 263.52 | 168.96 | 143.88 | 65.88 | 65.88 |
| average | | 1275.78 | 754.38 | 477.18 | 272.34 | 195.12 | 133.38 | 64.56 | 66.36 |
| 2 hour | Sample 2a | 1317.84 | 787.92 | 492.48 | 352.56 | 288.72 | 109.08 | 60 | 60 |
| 2 hour | Sample 2b | 1294.08 | 777.84 | 481.92 | 289.08 | 210 | 114.36 | 60 | 60 |
| average | | 1305.96 | 782.88 | 487.2 | 320.82 | 249.36 | 111.72 | 60 | 60 |

TABLE 8-continued

| Hydrogen Peroxide Concentration (ppm) with CA-400 Over Time | | | | | | | | | |
|---|---|---|---|---|---|---|---|---|---|
| | | Hydrogen Peroxide Concentration (ppm) Over Time (Seconds) | | | | | | | |
| Catalase Treatment | | 0 | 15 | 30 | 45 | 60 | 75 | 90 | 105 |
| 4 hour | Sample 4a | 1333.56 | 824.28 | 532.8 | 313.8 | 183.84 | 149.52 | 84.96 | 84.96 |
| 4 hour | Sample 4b | 1312.44 | 763.56 | 579 | 383.88 | 235.44 | 203.4 | 86.16 | 77.4 |
| average | | 1323 | 793.92 | 555.9 | 348.84 | 209.64 | 176.46 | 85.56 | 81.18 |
| Average Summary | | | | | | | | | |
| 0 hour | | 1308.66 | 725.28 | 448.2 | 309.3 | 209.64 | 140.94 | 58.8 | 58.8 |
| 1 hour | | 1275.78 | 754.38 | 477.18 | 272.34 | 195.12 | 133.38 | 64.56 | 66.36 |
| 2 hour | | 1305.96 | 782.88 | 487.2 | 320.82 | 249.36 | 111.72 | 60 | 60 |
| 4 hour | | 1323 | 793.92 | 555.9 | 348.84 | 209.64 | 176.46 | 85.56 | 81.18 |

Example 4 shows that CA-400 is stable at 60° C. over time because even after being in a hot water bath for four hours and exposed to 20,000 ppm acetic acid it is still capable of decreasing the concentration of hydrogen peroxide over time.

Example 5

Example 5 determined the temperature stability of the CA-100 catalase. For this example, a 5000 ppm sample of CA-100 was placed in a small glass vial and placed in a water bath at 60° C. Samples of the CA-100 were removed from the water bath and placed in an ice water bath after certain exposure times. After the ice water bath, the sample was tested against hydrogen peroxide at room temperature in a UV-VIS spectrophotometer at 240 nm for 2 minutes. A sample of the enzyme in distilled water was also run. The sample was prepared for the spectrophotometer by pipeting 3 ml of a stock solution of hydrogen peroxide into a 1 cm×1 cm quartz cuvette. 250 microliters of the catalase solution was added to the hydrogen peroxide solution. The spectrophotometer took measurements at 15 second intervals. The raw numbers are shown in Table 9. The adjusted numbers (raw catalase in hydrogen peroxide numbers—distilled water control) are shown in Table 10. The spectrophotometer measurements were converted into hydrogen peroxide concentration. These values were calculated in the same manner as outlined in example 3. The concentration of hydrogen peroxide (ppm) over time in shown in Table 11.

TABLE 9

| Spectrophotometer Measurements for CA-100 in Hydrogen Peroxide | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 1.2669 | 0.9803 | 0.7579 | 0.5633 | 0.4412 | 0.3634 | 0.3047 | 0.2776 |
| 0 hour | Sample 0b | 1.2179 | 0.8624 | 0.6725 | 0.5207 | 0.391 | 0.3345 | 0.2884 | 0.2533 |
| 1 hour | Sample 1a | 1.2046 | 0.8924 | 0.706 | 0.5422 | 0.4418 | 0.3606 | 0.3022 | 0.2607 |
| 1 hour | Sample 1b | 1.2256 | 0.8772 | 0.6772 | 0.5134 | 0.4253 | 0.3712 | 0.2619 | 0.1927 |
| 2 hour | Sample 2a | 1.228 | 0.8956 | 0.6639 | 0.4909 | 0.3791 | 0.3055 | 0.2364 | 0.2058 |
| 2 hour | Sample 2b | 1.231 | 0.8842 | 0.6521 | 0.4879 | 0.3753 | 0.2984 | 0.2488 | 0.1836 |
| 4 hour | Sample 4a | 1.2308 | 0.8825 | 0.6556 | 0.5265 | 0.3958 | 0.3103 | 0.2691 | 0.2019 |
| 4 hour | Sample 4b | 1.2265 | 0.893 | 0.6856 | 0.5394 | 0.3914 | 0.3213 | 0.2797 | 0.1937 |
| Distilled Water Control | | | | | | | | | |
| 0 hour | | 0.05 | | | | | | | |
| 1 hour | | 0.05 | | | | | | | |
| 2 hour | | 0.05 | | | | | | | |
| 4 hour | | 0.05 | | | | | | | |

TABLE 10

| Adjusted Spectrophotometer Measurements for CA-100 | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 1.2169 | 0.9303 | 0.7079 | 0.5133 | 0.3912 | 0.3134 | 0.2547 | 0.2276 |
| 0 hour | Sample 0b | 1.1679 | 0.8124 | 0.6225 | 0.4707 | 0.341 | 0.2845 | 0.2384 | 0.2033 |
| 1 hour | Sample 1a | 1.1546 | 0.8424 | 0.656 | 0.4922 | 0.3918 | 0.3106 | 0.2522 | 0.2107 |
| 1 hour | Sample 1b | 1.1756 | 0.8272 | 0.6272 | 0.4634 | 0.3753 | 0.3212 | 0.2119 | 0.1427 |
| 2 hour | Sample 2a | 1.178 | 0.8456 | 0.6139 | 0.4409 | 0.3291 | 0.2555 | 0.1864 | 0.1558 |
| 2 hour | Sample 2b | 1.181 | 0.8342 | 0.6021 | 0.4379 | 0.3253 | 0.2484 | 0.1988 | 0.1336 |
| 4 hour | Sample 4a | 1.1808 | 0.8325 | 0.6056 | 0.4765 | 0.3458 | 0.2603 | 0.2191 | 0.1519 |
| 4 hour | Sample 4b | 1.1765 | 0.843 | 0.6356 | 0.4894 | 0.3414 | 0.2713 | 0.2297 | 0.1437 |

TABLE 11

Hydrogen Peroxide Concentration (ppm) with CA-100 Over Time

| Catalase Treatment | | Hydrogen Peroxide Concentration (ppm) Over Time (Seconds) | | | | | | | |
|---|---|---|---|---|---|---|---|---|---|
| | | 0 | 15 | 30 | 45 | 60 | 75 | 90 | 105 |
| 0 hour | Sample 0a | 1460.28 | 1116.36 | 849.48 | 615.96 | 469.44 | 376.08 | 305.64 | 273.12 |
| 0 hour | Sample 0b | 1401.48 | 974.88 | 747 | 564.84 | 409.2 | 341.4 | 286.08 | 243.96 |
| average | | 1430.88 | 1045.62 | 798.24 | 590.4 | 439.32 | 358.74 | 295.86 | 258.54 |
| 1 hour | Sample 1a | 1385.52 | 1010.88 | 787.2 | 590.64 | 470.16 | 372.72 | 302.64 | 252.84 |
| 1 hour | Sample 1b | 1410.72 | 992.64 | 752.64 | 556.08 | 450.36 | 385.44 | 254.28 | 171.24 |
| average | | 1398.12 | 1001.76 | 769.92 | 573.36 | 460.26 | 379.08 | 278.46 | 212.04 |
| 2 hour | Sample 2a | 1413.6 | 1014.72 | 736.68 | 529.08 | 394.92 | 306.6 | 223.68 | 186.96 |
| 2 hour | Sample 2b | 1417.2 | 1001.04 | 722.52 | 525.48 | 390.36 | 298.08 | 238.56 | 160.32 |
| average | | 1415.4 | 1007.88 | 729.6 | 527.28 | 392.64 | 302.34 | 231.12 | 173.64 |
| 4 hour | Sample 4a | 1416.96 | 999 | 726.72 | 571.8 | 414.96 | 312.36 | 262.92 | 182.28 |
| 4 hour | Sample 4b | 1411.8 | 1011.6 | 762.72 | 587.28 | 409.68 | 325.56 | 275.64 | 172.44 |
| average | | 1414.38 | 1005.3 | 744.72 | 579.54 | 412.32 | 318.96 | 269.28 | 177.36 |
| Average Summary | | | | | | | | | |
| 0 hour | | 1430.88 | 1045.62 | 798.24 | 590.4 | 439.32 | 358.74 | 295.86 | 258.54 |
| 1 hour | | 1398.12 | 1001.76 | 769.92 | 573.36 | 460.26 | 379.08 | 278.46 | 212.04 |
| 2 hour | | 1415.4 | 1007.88 | 729.6 | 527.28 | 392.64 | 302.34 | 231.12 | 173.64 |
| 4 hour | | 1414.38 | 1005.3 | 744.72 | 579.54 | 412.32 | 318.96 | 269.28 | 177.36 |

Example 5 shows that CA-100 is stable at 60° C. over time because even after being in a hot water bath for four hours, it is still capable of decreasing the concentration of hydrogen peroxide.

Example 6

Example 6 determined the temperature stability of CA-100 catalase in the presence of 20,000 ppm acetic acid. For this example, a 5000 ppm sample of CA-100 along with 20000 ppm solution of acetic acid was placed in a small glass vial and placed in a water bath at 60° C. Samples of the CA-100 were removed from the water bath and placed in an ice water bath after certain exposure times. After the ice water bath, the sample was tested against hydrogen peroxide at room temperature in a UV-VIS spectrophotometer at 240 nm for 2 minutes. A sample of the enzyme in distilled water was also run. The sample was prepared for the spectrophotometer by pipeting 3 ml of a stock solution of hydrogen peroxide into a 1 cm×1 cm quartz cuvette. 250 microliters of the catalase solution was added to the hydrogen peroxide solution. The spectrophotometer took measurements at 15 second intervals. The raw numbers are shown in Table 12. The adjusted numbers (raw catalase in hydrogen peroxide numbers—distilled water control) are shown in Table 13. The spectrophotometer measurements were converted into hydrogen peroxide concentration as in example 3. The concentration of hydrogen peroxide (ppm) over time in shown in Table 14.

TABLE 12

Spectrophotometer Measurements for CA-100 in Hydrogen Peroxide

| Catalase Treatment | | Spectrophotometer Measurements Over Time (Seconds) | | | | | | | |
|---|---|---|---|---|---|---|---|---|---|
| | | 0 | 15 | 30 | 45 | 60 | 75 | 90 | 105 |
| 0 hour | Sample 0a | 1.1732 | 1.0802 | 1.0007 | 0.9116 | 0.8141 | 0.7138 | 0.6088 | 0.5273 |
| 0 hour | Sample 0b | 1.2786 | 1.1824 | 1.1099 | 1.0332 | 0.948 | 0.8053 | 0.6792 | 0.5832 |
| 1 hour | Sample 1a | 1.2264 | 1.159 | 1.0966 | 1.0234 | 0.9517 | 0.8671 | 0.7812 | 0.6857 |
| 1 hour | Sample 1b | 1.279 | 1.2317 | 1.1744 | 1.1077 | 0.9912 | 0.8737 | 0.7716 | 0.6764 |
| 2 hour | Sample 2a | 1.2504 | 1.1984 | 1.14 | 1.0692 | 0.989 | 0.8659 | 0.7645 | 0.6673 |
| 2 hour | Sample 2b | 1.2591 | 1.1768 | 1.1254 | 1.0524 | 0.9612 | 0.8588 | 0.7593 | 0.6646 |
| 4 hour | Sample 4a | 1.2635 | 1.1992 | 1.1345 | 1.0586 | 0.9685 | 0.8842 | 0.8004 | 0.7400 |
| 4 hour | Sample 4b | 1.2267 | 1.1643 | 1.1015 | 1.0278 | 0.9403 | 0.8584 | 0.7771 | 0.73 |
| Distilled Water Control | | | | | | | | | |
| 0 hour | | 0.05 | | | | | | | |
| 1 hour | | 0.05 | | | | | | | |
| 2 hour | | 0.05 | | | | | | | |
| 4 hour | | 0.05 | | | | | | | |

TABLE 13

Adjusted Spectrophotometer Measurements for CA-100

| Catalase Treatment | | Spectrophotometer Measurements Over Time (Seconds) | | | | | | | |
|---|---|---|---|---|---|---|---|---|---|
| | | 0 | 15 | 30 | 45 | 60 | 75 | 90 | 105 |
| 0 hour | Sample 0a | 1.1232 | 1.0302 | 0.9507 | 0.8616 | 0.7641 | 0.6638 | 0.5588 | 0.4773 |
| 0 hour | Sample 0b | 1.2286 | 1.1324 | 1.0599 | 0.9832 | 0.898 | 0.7553 | 0.6292 | 0.5332 |

TABLE 13-continued

| Adjusted Spectrophotometer Measurements for CA-100 | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 1 hour | Sample 1a | 1.1764 | 1.109 | 1.0466 | 0.9734 | 0.9017 | 0.8171 | 0.7312 | 0.6357 |
| 1 hour | Sample 1b | 1.229 | 1.1817 | 1.1244 | 1.0577 | 0.9412 | 0.8237 | 0.7216 | 0.6264 |
| 2 hour | Sample 2a | 1.2004 | 1.1484 | 1.09 | 1.0192 | 0.939 | 0.8159 | 0.7145 | 0.6173 |
| 2 hour | Sample 2b | 1.2091 | 1.1268 | 1.0754 | 1.0024 | 0.9112 | 0.8088 | 0.7093 | 0.6146 |
| 4 hour | Sample 4a | 1.2135 | 1.1492 | 1.0845 | 1.0086 | 0.9185 | 0.8342 | 0.7504 | 0.69 |
| 4 hour | Sample 4b | 1.1767 | 1.1143 | 1.0515 | 0.9778 | 0.8903 | 0.8084 | 0.7271 | 0.68 |

TABLE 14

| Hydrogen Peroxide Concentration (ppm) with CA-100 Over Time | | | | | | | | | |
|---|---|---|---|---|---|---|---|---|---|
| | | Hydrogen Peroxide Concentration (ppm) Over Time (Seconds) | | | | | | | |
| Catalase Treatment | | 0 | 15 | 30 | 45 | 60 | 75 | 90 | 105 |
| 0 hour | Sample 0a | 1347.84 | 1236.24 | 1140.84 | 1033.92 | 916.92 | 796.56 | 670.56 | 572.76 |
| 0 hour | Sample 0b | 1474.32 | 1358.88 | 1271.88 | 1179.84 | 1077.6 | 906.36 | 755.04 | 639.84 |
| average | | 1411.08 | 1297.56 | 1206.36 | 1106.88 | 997.26 | 851.46 | 712.8 | 606.3 |
| 1 hour | Sample 1a | 1411.68 | 1330.8 | 1255.92 | 1168.08 | 1082.04 | 980.52 | 877.44 | 762.84 |
| 1 hour | Sample 1b | 1474.8 | 1418.04 | 1349.28 | 1269.24 | 1129.44 | 988.44 | 865.92 | 751.68 |
| average | | 1443.24 | 1374.42 | 1302.6 | 1218.66 | 1105.74 | 984.48 | 871.68 | 757.26 |
| 2 hour | Sample 2a | 1440.48 | 1378.08 | 1308 | 1223.04 | 1126.8 | 979.08 | 857.4 | 740.76 |
| 2 hour | Sample 2b | 1450.92 | 1352.16 | 1290.48 | 1202.88 | 1093.44 | 970.56 | 851.16 | 737.52 |
| average | | 1445.7 | 1365.12 | 1299.24 | 1212.96 | 1110.12 | 974.82 | 854.28 | 739.14 |
| 4 hour | Sample 4a | 1456.20 | 1379.07 | 1301.45 | 1210.36 | 1102.21 | 1000.98 | 900.50 | 828 |
| 4 hour | Sample 4b | 1412.04 | 1337.16 | 1261.8 | 1173.36 | 1068.36 | 970.08 | 872.52 | 816 |
| average | | 1434.12 | 1358.12 | 1281.63 | 1191.86 | 1085.29 | 985.53 | 886.50 | 822 |
| Average Summary | | | | | | | | | |
| 0 hour | | 1411.08 | 1297.56 | 1206.36 | 1106.88 | 997.26 | 851.46 | 712.8 | 606.3 |
| 1 hour | | 1443.24 | 1374.42 | 1302.6 | 1218.66 | 1105.74 | 984.48 | 871.68 | 757.26 |
| 2 hour | | 1445.7 | 1365.12 | 1299.24 | 1212.96 | 1110.12 | 974.82 | 854.28 | 739.14 |
| 4 hour | | 1434.12 | 1358.12 | 1281.63 | 1191.86 | 1085.29 | 985.53 | 886.50 | 822 |

Example 6 shows that CA-100 is stable at 60° C. in the presence of 20,000 ppm acetic acid because even after being in a hot water bath for four hours, it is still capable of decreasing the concentration of hydrogen peroxide.

Example 7

Example 7 determined the temperature stability of the ASC Super G catalase. For this example, a 5000 ppm sample of ASC Super G was placed in a small glass vial and placed in a water bath at 60° C. Samples of the ASC Super G were removed from the water bath and placed in an ice water bath after certain exposure times. After the ice water bath, the sample was tested against hydrogen peroxide at room temperature in a UV-VIS spectrophotometer at 240 nm for 2 minutes. A sample of the enzyme in distilled water was also run. The sample was prepared for the spectrophotometer by pipeting 3 ml of a stock solution of hydrogen peroxide into a 1 cm×1 cm quartz cuvette. 250 microliters of the catalase solution was added to the hydrogen peroxide solution. The spectrophotometer took measurements at 15 second intervals. The raw numbers are shown in Table 15. The adjusted numbers (raw catalase in hydrogen peroxide numbers—distilled water control) are shown in Table 16. The spectrophotometer measurements were converted into hydrogen peroxide concentration as in example 3. The concentration of hydrogen peroxide (ppm) over time in shown in Table 17.

TABLE 15

| Spectrophotometer Measurements for ASC Super G in Hydrogen Peroxide | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 0.8948 | 0.47 | 0.3527 | 0.2502 | 0.1935 | 0.1716 | 0.1487 | 0.1405 |
| 0 hour | Sample 0b | 0.893 | 0.5036 | 0.3353 | 0.2488 | 0.1874 | 0.1619 | 0.151 | 0.1448 |
| 1 hour | Sample 1a | 0.926 | 0.548 | 0.3673 | 0.2708 | 0.1802 | 0.1458 | 0.1294 | 0.1215 |
| 1 hour | Sample 1b | 0.9145 | 0.5469 | 0.3647 | 0.2682 | 0.207 | 0.1535 | 0.1346 | 0.1243 |
| 2 hour | Sample 2a | 0.9291 | 0.5386 | 0.3373 | 0.2251 | 0.1707 | 0.143 | 0.1275 | 0.1196 |
| 2 hour | Sample 2b | 0.8786 | 0.5008 | 0.3625 | 0.3191 | 0.2292 | 0.1741 | 0.143 | 0.1287 |
| 4 hour | Sample 4a | 0.9226 | 0.5086 | 0.3752 | 0.2729 | 0.2103 | 0.1694 | 0.1444 | 0.1282 |
| 4 hour | Sample 4b | 0.9472 | 0.5584 | 0.3823 | 0.2684 | 0.1984 | 0.1579 | 0.1367 | 0.1249 |

TABLE 15-continued

| Spectrophotometer Measurements for ASC Super G in Hydrogen Peroxide | | | | | | | | |
|---|---|---|---|---|---|---|---|---|
| | Spectrophotometer Measurements Over Time (Seconds) | | | | | | | |
| Catalase Treatment | 0 | 15 | 30 | 45 | 60 | 75 | 90 | 105 |
| Distilled Water Control | | | | | | | | |
| 0 hour | 0.1024 | | | | | | | |
| 1 hour | 0.1024 | | | | | | | |
| 2 hour | 0.1024 | | | | | | | |
| 4 hour | 0.1024 | | | | | | | |

TABLE 16

| Adjusted Spectrophotometer Measurements for ASC Super G | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 0.7924 | 0.3676 | 0.2503 | 0.1478 | 0.0911 | 0.0692 | 0.0463 | 0.0381 |
| 0 hour | Sample 0b | 0.7906 | 0.4012 | 0.2329 | 0.1464 | 0.085 | 0.0595 | 0.0486 | 0.0424 |
| 1 hour | Sample 1a | 0.8236 | 0.4456 | 0.2649 | 0.1684 | 0.0778 | 0.0434 | 0.027 | 0.0191 |
| 1 hour | Sample 1b | 0.8121 | 0.4445 | 0.2623 | 0.1658 | 0.1046 | 0.0511 | 0.0322 | 0.0219 |
| 2 hour | Sample 2a | 0.8267 | 0.4362 | 0.2349 | 0.1227 | 0.0683 | 0.0406 | 0.0251 | 0.0172 |
| 2 hour | Sample 2b | 0.7762 | 0.3984 | 0.2601 | 0.2167 | 0.1268 | 0.0717 | 0.0406 | 0.0263 |
| 4 hour | Sample 4a | 0.8202 | 0.4062 | 0.2728 | 0.1705 | 0.1079 | 0.067 | 0.042 | 0.0258 |
| 4 hour | Sample 4b | 0.8448 | 0.456 | 0.2799 | 0.166 | 0.096 | 0.0555 | 0.0343 | 0.0225 |

TABLE 17

| Hydrogen Peroxide Concentration (ppm) with ASC Super G Over Time | | | | | | | | | |
|---|---|---|---|---|---|---|---|---|---|
| | | Hydrogen Peroxide Concentration (ppm) Over Time (Seconds) | | | | | | | |
| Catalase Treatment | | 0 | 15 | 30 | 45 | 60 | 75 | 90 | 105 |
| 0 hour | Sample 0a | 950.88 | 441.12 | 300.36 | 177.36 | 109.32 | 83.04 | 55.56 | 45.72 |
| 0 hour | Sample 0b | 948.72 | 481.44 | 279.48 | 175.68 | 102 | 71.4 | 58.32 | 50.88 |
| average | | 949.8 | 461.28 | 289.92 | 176.52 | 105.66 | 77.22 | 56.94 | 48.3 |
| 1 hour | Sample 1a | 988.32 | 534.72 | 317.88 | 202.08 | 93.36 | 52.08 | 32.4 | 22.92 |
| 1 hour | Sample 1b | 974.52 | 533.4 | 314.76 | 198.96 | 125.52 | 61.32 | 38.64 | 26.28 |
| average | | 981.42 | 534.06 | 316.32 | 200.52 | 109.44 | 56.7 | 35.52 | 24.6 |
| 2 hour | Sample 2a | 992.04 | 523.44 | 281.88 | 147.24 | 81.96 | 48.72 | 30.12 | 20.64 |
| 2 hour | Sample 2b | 931.44 | 478.08 | 312.12 | 260.04 | 152.16 | 86.04 | 48.72 | 31.56 |
| average | | 961.74 | 500.76 | 297 | 203.64 | 117.06 | 67.38 | 39.42 | 26.1 |
| 4 hour | Sample 4a | 984.24 | 487.44 | 327.36 | 204.6 | 129.48 | 80.4 | 50.4 | 30.96 |
| 4 hour | Sample 4b | 1013.76 | 547.2 | 335.88 | 199.2 | 115.2 | 66.6 | 41.16 | 27 |
| average | | 999 | 517.32 | 331.62 | 201.9 | 122.34 | 73.5 | 45.78 | 28.98 |
| Average Summary | | | | | | | | | |
| | 0 hour | 949.8 | 461.28 | 289.92 | 176.52 | 105.66 | 77.22 | 56.94 | 48.3 |
| | 1 hour | 981.42 | 534.06 | 316.32 | 200.52 | 109.44 | 56.7 | 35.52 | 24.6 |
| | 2 hour | 961.74 | 500.76 | 297 | 203.64 | 117.06 | 67.38 | 39.42 | 26.1 |
| | 4 hour | 999 | 517.32 | 331.62 | 201.9 | 122.34 | 73.5 | 45.78 | 28.98 |

Example 7 shows that ASC Super G is stable at 60° C. over time because even after being in a hot water bath for four hours, it is still capable of decreasing the concentration of hydrogen peroxide.

Example 8

Example 8 determined the temperature stability of ASC Super G catalase in the presence of 20,000 ppm acetic acid. For this example, a 5000 ppm sample of ASC Super G along with 20000 ppm acetic acid was placed in a small glass vial and placed in a water bath at 60° C. Samples of the ASC Super G were removed from the water bath and placed in an ice water bath after certain exposure times. After the ice water bath, the sample was tested against hydrogen peroxide at room temperature in a UV-VIS spectrophotometer at 240 nm for 2 minutes. A sample of the enzyme in distilled water was also run. The sample was prepared for the spectrophotometer by pipeting 3 ml of a stock solution of hydrogen peroxide into a 1 cm×1 cm quartz cuvette. 250 microliters of the catalase solution was added to the hydrogen peroxide solution. The spectrophotometer took measurements at 15 second intervals. The raw numbers are shown in Table 18. The adjusted numbers (raw catalase in hydrogen peroxide numbers—distilled water control) are shown in Table 19. The spectrophotometer measurements were converted into hydrogen peroxide concentration. The concentration of hydrogen peroxide (ppm) over time in shown in Table 20.

TABLE 18

| Spectrophotometer Measurements for ASC Super G in Hydrogen Peroxide | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 1.1722 | 0.8785 | 0.6452 | 0.4711 | 0.3612 | 0.2926 | 0.2532 | 0.2347 |
| 0 hour | Sample 0b | 1.144 | 0.869 | 0.6519 | 0.483 | 0.3673 | 0.2946 | 0.24 | 0.211 |
| 1 hour | Sample 1a | 1.1493 | 0.8613 | 0.6326 | 0.4619 | 0.3542 | 0.2869 | 0.2483 | 0.2301 |
| 1 hour | Sample 1b | 1.1216 | 0.8528 | 0.6392 | 0.4736 | 0.3601 | 0.2889 | 0.236 | 0.2077 |
| 2 hour | Sample 2a | 1.1432 | 0.892 | 0.6904 | 0.5384 | 0.4112 | 0.3292 | 0.2765 | 0.241 |
| 2 hour | Sample 2b | 1.1536 | 0.8931 | 0.6885 | 0.5201 | 0.4302 | 0.3277 | 0.2654 | 0.2217 |
| 4 hour | Sample 4a | 1.1361 | 0.8821 | 0.6816 | 0.545 | 0.4524 | 0.3902 | 0.3492 | 0.3295 |
| 4 hour | Sample 4b | 1.1187 | 0.8516 | 0.633 | 0.4736 | 0.364 | 0.2861 | 0.2325 | 0.1972 |
| Distilled Water Control | | | | | | | | | |
| 0 hour | | 0.1024 | | | | | | | |
| 1 hour | | 0.1024 | | | | | | | |
| 2 hour | | 0.1024 | | | | | | | |
| 4 hour | | 0.1024 | | | | | | | |

TABLE 19

| Adjusted Spectrophotometer Measurements for ASC Super G | | | | | | | | | |
|---|---|---|---|---|---|---|---|---|---|
| | | Spectrophotometer Measurements Over Time (Seconds) | | | | | | | |
| Catalase Treatment | | 0 | 15 | 30 | 45 | 60 | 75 | 90 | 105 |
| 0 hour | Sample 0a | 1.0698 | 0.7761 | 0.5428 | 0.3687 | 0.2588 | 0.1902 | 0.1508 | 0.1323 |
| 0 hour | Sample 0b | 1.0416 | 0.7666 | 0.5495 | 0.3806 | 0.2649 | 0.1922 | 0.1376 | 0.1086 |
| 1 hour | Sample 1a | 1.0469 | 0.7589 | 0.5302 | 0.3595 | 0.2518 | 0.1845 | 0.1459 | 0.1277 |
| 1 hour | Sample 1b | 1.0192 | 0.7504 | 0.5368 | 0.3712 | 0.2577 | 0.1865 | 0.1336 | 0.1053 |
| 2 hour | Sample 2a | 1.0408 | 0.7896 | 0.588 | 0.436 | 0.3088 | 0.2268 | 0.1741 | 0.1386 |
| 2 hour | Sample 2b | 1.0512 | 0.7907 | 0.5861 | 0.4177 | 0.3278 | 0.2253 | 0.163 | 0.1193 |
| 4 hour | Sample 4a | 1.0337 | 0.7797 | 0.5792 | 0.4426 | 0.35 | 0.2878 | 0.2468 | 0.2271 |
| 4 hour | Sample 4b | 1.0163 | 0.7492 | 0.5306 | 0.3712 | 0.2616 | 0.1837 | 0.1301 | 0.0948 |

TABLE 20

| Hydrogen Peroxide Concentration (ppm) with ASC Super G Over Time | | | | | | | | | |
|---|---|---|---|---|---|---|---|---|---|
| | | Hydrogen Peroxide Concentration (ppm) Over Time (Seconds) | | | | | | | |
| Catalase Treatment | | 0 | 15 | 30 | 45 | 60 | 75 | 90 | 105 |
| 0 hour | Sample 0a | 1283.76 | 931.32 | 651.36 | 442.44 | 310.56 | 228.24 | 180.96 | 158.76 |
| 0 hour | Sample 0b | 1249.92 | 919.92 | 659.4 | 456.72 | 317.88 | 230.64 | 165.12 | 130.32 |
| average | | 1266.84 | 925.62 | 655.38 | 449.58 | 314.22 | 229.44 | 173.04 | 144.54 |
| 1 hour | Sample 1a | 1256.28 | 910.68 | 636.24 | 431.4 | 302.16 | 221.4 | 175.08 | 153.24 |
| 1 hour | Sample 1b | 1223.04 | 900.48 | 644.16 | 445.44 | 309.24 | 223.8 | 160.32 | 126.36 |
| average | | 1239.66 | 905.58 | 640.2 | 438.42 | 305.7 | 222.6 | 167.7 | 139.8 |
| 2 hour | Sample 2a | 1248.96 | 947.52 | 705.6 | 523.2 | 370.56 | 272.16 | 208.92 | 166.32 |
| 2 hour | Sample 2b | 1261.44 | 948.84 | 703.32 | 501.24 | 393.36 | 270.36 | 195.6 | 143.16 |
| average | | 1255.2 | 948.18 | 704.46 | 512.22 | 381.96 | 271.26 | 202.26 | 154.74 |
| 4 hour | Sample 4a | 1240.44 | 935.64 | 695.04 | 531.12 | 420 | 345.36 | 296.16 | 272.52 |
| 4 hour | Sample 4b | 1219.56 | 899.04 | 636.72 | 445.44 | 313.92 | 220.44 | 156.12 | 113.76 |
| average | | 1230 | 917.34 | 665.88 | 488.28 | 366.96 | 282.9 | 226.14 | 193.14 |
| Average Summary | | | | | | | | | |
| 0 hour | | 1266.84 | 926.62 | 655.38 | 449.58 | 314.22 | 229.44 | 173.04 | 144.54 |
| 1 hour | | 1239.66 | 905.58 | 640.2 | 438.42 | 305.7 | 222.6 | 167.7 | 139.8 |
| 2 hour | | 1255.2 | 948.18 | 704.46 | 512.22 | 381.96 | 271.26 | 202.26 | 154.74 |
| 4 hour | | 1230 | 917.34 | 665.88 | 488.28 | 366.96 | 282.9 | 226.14 | 193.14 |

Example 8 shows that ASC Super G is stable at 60° C. in the presence of 20,000 ppm acetic acid because even after being in a hot water bath for four hours, it is still capable of decreasing the concentration of hydrogen peroxide.

Example 9

Example 9 determined the effect of sequential addition of CA-100 catalase versus bulk addition of CA-100 catalase. For this example a 10 wt. % enzyme stock solution was prepared. A peracid concentrate was also prepared which included 13.5% peracetic acid, 10.88% hydrogen peroxide, and 23.15% acetic acid. The peracid concentrate was diluted to form a solution with about 3000 ppm peracetic acid. Additional glacial acetic acid was added to the diluted solution to bring the total acetic acid concentration to 20,000 ppm.

To test the effect of sequential addition, 1 ml of the enzyme stock solution (100 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate. After 30 minutes, another 1 ml of the enzyme stock solution (100 ppm enzyme for a total of 200 ppm enzyme) was added to the diluted peracid solution and titrated again.

To test the effect of bulk addition, 2 ml of the enzyme stock solution (200 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate.

TABLE 21

Sequential Addition of 2 ml of Enzyme

| Time | POAA titration | H2O2 titration | ppm POAA | ppm H2O2 |
|---|---|---|---|---|
| Test #1 -- Addition of 1 ml enzyme stock solution | | | | |
| 0 | 8.5 | 23.5 | 3230 | 2550 |
| 5 | 8.5 | 22.5 | 3230 | 2380 |
| 10 | 8.5 | 22.5 | 3230 | 2380 |
| 15 | 8.5 | 22.5 | 3230 | 2380 |
| 30 | 8.5 | 22.5 | 3230 | 2380 |
| Test #2 -- Second addition of 1 ml enzyme stock solution | | | | |
| 0 | 8.5 | 22.5 | 3230 | 2380 |
| 5 | 8.5 | 16.1 | 3230 | 1292 |
| 10 | 8.5 | 14 | 3230 | 935 |
| 15 | 8.5 | 12.85 | 3230 | 739.5 |
| 30 | 8.5 | 11.75 | 3230 | 552.5 |

TABLE 22

Bulk Addition of 2 ml of Enzyme

| Time | POAA titration | H2O2 titration | ppm POAA | ppm H2O2 |
|---|---|---|---|---|
| 0 | 8.4 | 23.1 | 3192 | 2499 |
| 5 | 8.4 | 14.6 | 3192 | 1054 |
| 10 | 8.4 | 12.1 | 3192 | 629 |
| 15 | 8.4 | 11.3 | 3192 | 493 |
| 30 | 8.4 | 10.25 | 3192 | 314.5 |
| 60 | 8.3 | 9.1 | 3154 | 136 |

Example 9 shows that in the case of CA-100 bulk addition is better at decreasing the hydrogen peroxide concentration than sequential addition because the bulk addition decreased the hydrogen peroxide concentration to 136 ppm compared to the 552.5 ppm of the sequential addition.

Example 10

Example 10 determined the effect of sequential addition of CA-400 catalase versus bulk addition of CA-400 catalase. For this example a 2 wt. % enzyme stock solution was prepared. A peracid concentrate was also prepared the included 13.5% peracetic acid, 10.88% hydrogen peroxide, and 23.15% acetic acid. The peracid concentrate was diluted to form a solution with 3000 ppm peracetic acid. Additional glacial acetic acid was added to the diluted solution to bring the total acetic acid concentration to 20,000 ppm.

To test the effect of sequential addition, 2 ml of the enzyme stock solution (40 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate. After 30 minutes, another 2 ml of the enzyme stock solution (40 ppm enzyme for a total of 80 ppm enzyme) was added to the diluted peracid solution and titrated again.

To test the effect of bulk addition, 4 ml of the enzyme stock solution (80 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate.

TABLE 23

Sequential Addition of 2 ml of Enzyme

| Time | POAA titration | H2O2 titration | ppm POAA | ppm H2O2 |
|---|---|---|---|---|
| Test #1 -- Addition of 2 ml enzyme stock solution | | | | |
| 0 | 8.6 | 23.45 | 3268 | 2524.5 |
| 5 | 8.6 | 18.1 | 3268 | 1615 |
| 10 | 8.6 | 16.6 | 3268 | 1360 |
| 15 | 8.6 | 15.5 | 3268 | 1173 |
| 30 | 8.6 | 15.3 | 3268 | 1139 |
| Test #2 -- Second addition of 2 ml enzyme stock solution | | | | |
| 0 | 8.6 | 15.3 | 3268 | 1139 |
| 5 | 8.6 | 11.8 | 3268 | 544 |
| 10 | 8.6 | 10.5 | 3268 | 323 |
| 15 | 8.6 | 9.8 | 3268 | 204 |
| 30 | 8.6 | 9.2 | 3268 | 102 |

TABLE 24

Bulk Addition of 4 ml of Enzyme

| Time | POAA titration | H2O2 titration | ppm POAA | ppm H2O2 |
|---|---|---|---|---|
| 0 | 8.5 | 23.1 | 3230 | 2482 |
| 5 | 8.5 | 17.1 | 3230 | 1462 |
| 10 | 8.5 | 15.9 | 3230 | 1258 |
| 15 | 8.5 | 14.8 | 3230 | 1071 |
| 30 | 8.5 | 13.5 | 3230 | 850 |
| 60 | 8.5 | 11.7 | 3230 | 544 |

Example 10 shows that in the case of CA-400 sequential addition is better at decreasing the hydrogen peroxide concentration than bulk addition because the sequential addition decreased the hydrogen peroxide concentration to 102 ppm compared to the 544 ppm of the bulk addition.

Example 11

Example 11 determined the effect of sequential addition of ASC Super G catalase versus bulk addition of ASC Super G catalase. For this example a 10 wt. % enzyme stock solution was prepared. A peracid concentrate was also prepared the included 13.5% peracetic acid, 10.88% hydrogen peroxide, and 23.15% acetic acid. The peracid concentrate was diluted to form a solution with 3000 ppm peracetic acid. Additional glacial acetic acid was added to the diluted solution to bring the total acetic acid concentration to 20,000 ppm.

To test the effect of sequential addition, 1 ml of the enzyme stock solution (100 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate. After 30 minutes, another 1 ml of the enzyme stock solution (100 ppm enzyme for a total of 200 ppm enzyme) was added to the diluted peracid solution and titrated again.

To test the effect of bulk addition, 2 ml of the enzyme stock solution (200 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate.

TABLE 25

Sequential Addition of 2 ml of Enzyme

| Time | POAA titration | H2O2 titration | ppm POAA | ppm H2O2 |
|---|---|---|---|---|
| Test #1 -- Addition of 1 ml enzyme stock solution | | | | |
| 0 | 8.5 | 23.45 | 3230 | 2541.5 |
| 5 | 8.5 | 20.9 | 3230 | 2108 |
| 10 | 8.5 | 20 | 3230 | 1955 |
| 15 | 8.5 | 19.5 | 3230 | 1870 |
| 30 | 8.5 | 19 | 3230 | 1785 |
| Test #2 -- Second addition of 1 ml enzyme stock solution | | | | |
| 0 | 8.5 | 19 | 3230 | 1785 |
| 5 | 8.5 | 14.8 | 3230 | 1071 |
| 10 | 8.5 | 11.8 | 3230 | 561 |
| 15 | 8.5 | 10.4 | 3230 | 323 |
| 30 | 8.5 | 9.5 | 3230 | 170 |

TABLE 26

Bulk Addition of 2 ml of Enzyme

| Time | POAA titration | H2O2 titration | ppm POAA | ppm H2O2 |
|---|---|---|---|---|
| 0 | 8.45 | 22.75 | 3211 | 2431 |
| 5 | 8.4 | 13.55 | 3192 | 875.5 |
| 10 | 8.4 | 11.7 | 3192 | 561 |
| 15 | 8.4 | 11.05 | 3192 | 450.5 |
| 30 | 8.4 | 10.3 | 3192 | 323 |
| 60 | 8.4 | 9.5 | 3192 | 187 |

Example 11 shows that in the case of ASC Super G sequential addition is better at decreasing the hydrogen peroxide concentration than bulk addition because the sequential addition decreased the hydrogen peroxide concentration to 170 ppm compared to the 187 ppm of the bulk addition.

Example 12

Example 12 determined the effect of sequential addition of ASC Super 200 catalase versus bulk addition of ASC Super 200 catalase. For this example a 2 wt. % enzyme stock solution was prepared. A peracid concentrate was also prepared the included 13.5% peracetic acid, 10.88% hydrogen peroxide, and 23.15% acetic acid. The peracid concentrate was diluted to form a solution with 3000 ppm peracetic acid. Additional glacial acetic acid was added to the diluted solution to bring the total acetic acid concentration to 20,000 ppm.

To test the effect of sequential addition, 2 ml of the enzyme stock solution (40 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate. After 30 minutes, another 2 ml of the enzyme stock solution (40 ppm enzyme for a total of 80 ppm enzyme) was added to the diluted peracid solution and titrated again.

To test the effect of bulk addition, 4 ml of the enzyme stock solution (80 ppm enzyme) was added to 1000 ml of the diluted peracid solution. The enzyme and peracid solution was put into a water bath at 50° C. and stirred with a magnetic stirrer. The solution was titrated for peracetic acid and hydrogen peroxide using an iodometric titration with 0.1N sodium thiosulfate.

TABLE 27

Sequential Addition of 2 ml of Enzyme

| Time | POAA titration | H2O2 titration | ppm POAA | ppm H2O2 |
|---|---|---|---|---|
| Test #1 - Addition of 1 ml enzyme stock solution | | | | |
| 0 | 8.5 | 23.5 | 3230 | 2550 |
| 5 | 8.5 | 15.75 | 3230 | 1232.5 |
| 10 | 8.5 | 13.45 | 3230 | 841.5 |
| 15 | 8.5 | 12.2 | 3230 | 629 |
| 30 | 8.5 | 10.9 | 3230 | 408 |
| Test #2 -- Second addition of 1 ml enzyme stock solution* | | | | |
| 0 | 8.5 | 18.7 | 3230 | 1734 |
| 5 | 8.5 | 9.4 | 3230 | 153 |
| 10 | 8.5 | 8.55 | 3230 | 8.5 |
| 15 | 8.5 | 8.5 | 3230 | 0 |
| 30 | 8.5 | 8.5 | 3230 | 0 |

*Note:
added~1000 ppm H2O2 to bring level up to more reasonable concentration for second enzyme addition

TABLE 28

Bulk Addition of 2 ml of Enzyme

| Time | POAA titration | H2O2 titration | ppm POAA | ppm H2O2 |
|---|---|---|---|---|
| 0 | 8.5 | 22.85 | 3230 | 2439.5 |
| 5 | 8.5 | 13.9 | 3230 | 918 |
| 10 | 8.5 | 12.2 | 3230 | 629 |
| 15 | 8.5 | 11.05 | 3230 | 433.5 |
| 30 | 8.5 | 10.4 | 3230 | 323 |
| 60 | 8.5 | 9.6 | 3230 | 187 |

Example 12 shows that in the case of ASC Super 200 sequential addition is better at decreasing the hydrogen peroxide concentration than bulk addition because the sequential addition decreased the hydrogen peroxide concentration to 0 ppm compared to the 187 ppm of the bulk addition even with the addition of additional H2O2 to the solution prior to the second addition of enzyme.

Example 13

Example 13 provides a contrast between how a conventional equilibrium peracid chemistry performs as an antimicrobial relative to that same chemistry with the addition of the ASC super 200 catalase described in the examples outlined above.

The test solutions outlined below were made up to a concentration of 2000 ppm active peracid from the 13.5% peracid concentrate outlined in example 9.

A 500 ml aliquot of this solution was treated with 0.25 g of ASC super 200. The remaining solution was untreated.

Both of these solutions were heated to 50° C. Three different spore crops were tested against each of these solutions to show how each efficacious each solution was over various periods of contact time.

TABLE 29

| Test Solutions | | | | |
|---|---|---|---|---|
| Test Substance | Concentration | Grams of Test Substance | Diluent | Amount of Diluent |
| POAA | 2000 ppm POAA | 14.8 g T100 POAA | 500 ppm Hard Water | To 1000 mL |
| Peracid plus catalase | 2000 ppm POAA | 500 g of POAA solution<br>0.25 g ASC super 200 catalase | NA | NA |

TABLE 30

Efficacy Against *Bacillus cereus* BC896CB

| Test Substance | Exposure Time | Trial 1 Survivors (CFU/mL) | Trial 2 Survivors (CFU/mL) | Average Survivors (CFU/mL) | Log Reduction | Percent Reduction |
|---|---|---|---|---|---|---|
| Peracid alone | 10 sec | $2.2 \times 10^5$ | $2.3 \times 10^5$ | $2.2 \times 10^5$ | 0.41 | 61.207 |
| | 30 sec | $8.5 \times 10^4$ | $7.5 \times 10^4$ | $8.0 \times 10^4$ | 0.86 | 86.207 |
| | 1 min | $1.9 \times 10^4$ | $1.5 \times 10^4$ | $1.7 \times 10^4$ | 1.53 | 97.069 |
| | 2 min | $1.1 \times 10^3$ | $2.3 \times 10^3$ | $1.7 \times 10^3$ | 2.53 | 99.707 |
| Peracid plus catalase | 10 sec | <10 | <10 | <10 | >4.76 | >99.998 |
| | 30 sec | <10 | <10 | <10 | >4.76 | >99.998 |
| | 1 min | <10 | <10 | <10 | >4.76 | >99.998 |
| | 2 min | <10 | <10 | <10 | >4.76 | >99.998 |

TABLE 31

Efficacy Against *Bacillus thuringensis* ATCC 10792

| Test Substance | Exposure Time | Trial 1 Survivors (CFU/mL) | Trial 2 Survivors (CFU/mL) | Average Survivors (CFU/mL) | Log Reduction | Percent Reduction |
|---|---|---|---|---|---|---|
| Peracid alone | 10 sec | $1.0 \times 10^4$ | $1.9 \times 10^4$ | $1.4 \times 10^4$ | 0.68 | 79.286 |
| | 30 sec | $6.6 \times 10^2$ | $7.1 \times 10^2$ | $6.8 \times 10^2$ | 2.01 | 99.021 |
| | 1 min | <10 | $1 \times 10^1$ | <10 | >3.85 | >99.986 |
| | 2 min | <10 | $2 \times 10^1$ | $<1.5 \times 10^1$ | >3.67 | >99.979 |
| Peracid plus catalase | 10 sec | <10 | <10 | <10 | >3.85 | >99.986 |
| | 30 sec | $8 \times 10^1$ | <10 | $4.5 \times 10^1$ | >3.19 | >99.936 |
| | 1 min | <10 | <10 | <10 | >3.85 | >99.986 |
| | 2 min | <10 | <10 | <10 | >3.85 | >99.986 |

TABLE 32

Efficacy Against *Bacillus thuringensis* ATCC 33679

| Test Substance | Exposure Time | Trial 1 Survivors (CFU/mL) | Trial 2 Survivors (CFU/mL) | Average Survivors (CFU/mL) | Log Reduction | Percent Reduction |
|---|---|---|---|---|---|---|
| Peracid alone | 10 sec | $2.0 \times 10^4$ | $1.2 \times 10^4$ | $1.6 \times 10^4$ | 0.64 | 77.143 |
| | 30 sec | $2 \times 10^1$ | $6 \times 10^1$ | $4.0 \times 10^1$ | 3.24 | 99.943 |
| | 1 min | $7 \times 10^3$ | <10 | $<3.5 \times 10^3$ | 1.30 | 94.993 |
| | 2 min | <10 | <10 | <10 | >3.85 | >99.986 |
| Peracid plus catalase | 10 sec | $1.9 \times 10^2$ | <10 | <100 | >2.85 | >99.857 |
| | 30 sec | <10 | <10 | <10 | >3.85 | >99.986 |
| | 1 min | <10 | <10 | <10 | >3.85 | >99.986 |
| | 2 min | <10 | <10 | <10 | >3.85 | >99.986 |

The result clearly show the positive impact of the combined catalase peracid composition relative to the native POAA solution.

Example 14

A second key feature of this technology is its ability to meet the efficacy requirements for aseptic packaging applications at reduced temperatures.

The test requirements in this case related to a carrier test. The carrier test entails drying an innoculum of spores down onto a small cylindrical carrier. These carriers are then placed into a test solution of antimicrobial for a set period of time. They are then removed from the solution, neutralized and dropped in series into a set of nutrient containing growth tubes. Growth or lack of growth in these tubes is a measure of the efficacy of the detergent.

This example tested a 3000 ppm solution of POAA treated with ~100 ppm ASC super 200 as well as that same solution without addition of this enzyme. Test conditions were 19 seconds of exposure to the chemistry with the chemistry being held @50 or 60° C.

TABLE 33

Efficacy Against *Clostridium sporogenes* ATCC 3584

| Test Substance | Concentration of POAA | Exposure Temp (° C.) | # 1° Negative Tubes/ # 1° Tubes Tested | # 2° Negative Tubes/ # 2° Tubes Tested |
|---|---|---|---|---|
| Peracid plus ASC Super 200 | 3000 ppm | 50 | 60/60 | 60/60 |
| Peracid plus ASC Super 200 | 3000 ppm | 60 | 60/60 | 60/60 |
| Peracid | 3000 ppm | 55 | 57/60 | 57/60 |
| Peracid | 3000 ppm | 60 | 59/60 | 59/60 |

Passing for this test is 60/60. These result show the advantage of inclusion of the catalase for this application.

Example 15

Example 15 shows the accumulation of hydrogen peroxide over time with a without catalase. For this example, 3000 and 6000 ppm solutions of peroxyacetic acid were made from a commercially available peracid concentrate containing about 10% POAA and about 10% hydrogen peroxide. These solutions were split. Half treated with the ASC super G catalase enzyme and the other half was left untreated. Both solutions were placed in a 60° C. water bath and were monitored for changes in peroxide concentration over time.

Table 34 outlines the results of this experiment. Examples 34a and 34b represent an untreated peracid solution. Examples 34c and 34d represent those same peracid solutions treated with a catalase enzyme after the time 0 measurement to bring the peroxide level to 0.

TABLE 34

| H2O2 at Exposure Time, hrs @ 60 deg C. | 0 | 1.5 | 3 | 7 |
|---|---|---|---|---|
| 34a. 3000 ppm POAA | 3020 | 3140 | 3250 | 3490 |
| 34b. 6000 ppm POAA | 5910 | 6220 | 6560 | 7130 |
| 34c. 3000 ppm POAA + catalase | 3020 | 120 | 260 | 460 |
| 34d. 6000 ppm POAA + catalase | 5910 | 320 | 650 | 1200 |

Examples 34a and 34b show the natural accumulation of peroxide that follows dilution of a peracid concentrate. Examples 34c and 34d show that same effect with a peracid solution that has had all of the peroxide eliminated through catalytic reaction. These results demonstrate that the preferred range of peroxide and peracid can only be maintained when combined with the addition of catalase enzyme.

Definitions

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

The use of the terms "antimicrobial" in this application does not mean that any resulting products are approved for use as an antimicrobial agent.

The foregoing summary, detailed description, and examples provide a sound basis for understanding the invention, and some specific example embodiments of the invention. Since the invention can comprise a variety of embodiments, the above information is not intended to be limiting. The invention resides in the claims.

What is claimed is:

1. A method of disinfecting packages through aseptic packaging comprising (a) providing an antimicrobial composition at a point of use comprising (i) from about 20 ppm to about 250 ppm of a catalase enzyme selected from the group consisting of bovine derived catalase, fungal derived catalase, and mixtures thereof, wherein the catalase maintains 50% of its activity over a period of one hour at a pH from about 2.0 to about 2.5;

(ii) from about 0.00001% to about 0.5 wt. % hydrogen peroxide;

(iii) from about 0.1% to about 20.0 wt. % of a $C_1$-$C_{10}$ carboxylic acid; and (iv) from about 0.1% to about 2.0 wt. % of a $C_1$-$C_{10}$percarboxylic acid; and (b) applying the antimicrobial composition to a surface of a food package at a temperature of about 20° C. to about 40° C. in an amount sufficient to render a final food product located in the food package suitable for distribution and sale under nonrefrigerated storage conditions.

2. The method of claim 1, wherein the catalase enzyme is able to degrade at least 500 ppm of the hydrogen peroxide in less than 15 minutes.

3. The method of claim 1, wherein the catalase maintains 50% of its initial catalytic activity over a period of 1 hour at a temperature between 20° C. and 40° C. and a pH from about 2.0 to about 2.5.

4. The method of claim 1, wherein the catalase is added to the antimicrobial composition in bulk addition.

5. The method of claim 1, wherein the catalase is added to the antimicrobial composition in serial applications.

6. The method of claim 1, wherein the catalase is free floating in the antimicrobial composition.

7. The method of claim 1, wherein the catalase is immobilized on a water insoluble substrate that is in contact with the remaining antimicrobial composition.

8. The method of claim 1, wherein the hydrogen peroxide concentration remains below 1000 ppm.

9. The method of claim 1, wherein the carboxylic acid is selected from the group consisting of acetic acid, octanoic acid, and mixtures thereof, and the percarboxylic acid is selected from the group consisting of peracetic acid, peroctanoic acid, and mixtures thereof.

10. A method of disinfecting packages through aseptic packaging comprising (a) providing an antimicrobial composition comprising from about 20 ppm to about 250 ppm of a fungal derived catalase enzyme, wherein the catalase maintains 50% of its activity over a period of one hour at a pH from about 2.0 to about 2.5;

(ii) from about 0.00001% to about 0.3 wt. % hydrogen peroxide;

(iii) from about 0.1% to about 2.0 wt. % of a carboxylic acid selected from the group consisting of acetic acid, octanoic acid, and mixtures thereof; and (iv) from about 0.15% to about 0.4 wt. % of a percarboxylic acid selected from the group consisting of peracetic acid, peroctanoic acid, and mixtures thereof; and (b) applying the antimicrobial composition to a surface of a food package at a temperature from about 20° C. to about 40° C. in an amount sufficient to render a final food product located in the food package suitable for distribution and sale under nonrefrigerated storage conditions.

11. The method of claim 10, further comprising collecting the antimicrobial composition after it has been applied to the surface of the food package and using the collected composition for a different purpose.

12. The method of claim 10, wherein the antimicrobial composition is applied to a surface of a food package by spraying for at least 5 seconds.

13. The method of claim 10, wherein the antimicrobial composition is applied to a surface of a food package by flooding for at least 5 seconds.

14. The method of claim 10, wherein the food package is a material selected from the group consisting of polyethylene terephthalate, high density polyethylene, polypropylene, low density polyethylene, polycarbonate, polyvinyl alcohol, aluminum, paperboard, steel, glass, and combinations thereof.

15. The method of claim 14, wherein the food package is selected from the group consisting of a film, a pouch, and a bottle.

16. The method of claim 10, wherein the antimicrobial composition is applied to a food package once.

17. The method of claim 10, wherein the antimicrobial composition is re-used.

18. The method of claim 10, wherein the catalase enzyme is a fungal derived catalase.

* * * * *